US008771707B2

(12) United States Patent
Chapman et al.

(10) Patent No.: US 8,771,707 B2
(45) Date of Patent: Jul. 8, 2014

(54) BOTULINUM NEUROTOXIN E RECEPTORS AND USES THEREOF

(75) Inventors: Edwin R. Chapman, Madison, WI (US); Min Dong, Southborough, MA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 973 days.

(21) Appl. No.: 12/569,905

(22) Filed: Sep. 30, 2009

(65) Prior Publication Data

US 2010/0104560 A1  Apr. 29, 2010

Related U.S. Application Data

(60) Provisional application No. 61/101,421, filed on Sep. 30, 2008.

(51) Int. Cl.
*A61K 39/08* (2006.01)
*A61K 38/02* (2006.01)

(52) U.S. Cl.
USPC .................................... 424/239.1; 424/184.1

(58) Field of Classification Search
None
See application file for complete search history.

(56) References Cited

U.S. PATENT DOCUMENTS

| | | | | |
|---|---|---|---|---|
| 2004/0204388 A1* | 10/2004 | Lynch et al. | ................ | 514/151 |
| 2008/0220456 A1* | 9/2008 | Williams et al. | ............. | 435/7.32 |
| 2009/0252722 A1* | 10/2009 | Mahrhold et al. | ......... | 424/130.1 |
| 2010/0249372 A1* | 9/2010 | Chapman et al. | ............ | 530/322 |

OTHER PUBLICATIONS

Dong et al (Mol Biol Cell 19: 5226-5237, 2008).*
Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Skolnick et al., 2000, Trends in Biotech. 18(1):34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Charlesworth et al (JBC 262: 13409-13416, 1987).*
Bajjalieh et al. (Science 257: 1271-1273, 1992).*
Humeau et al (Biochimie 82: 427-446, 2000).*
Dolly, et al., "Acceptors for botulinum neurotoxin reside on motor nerve terminals and mediate its internalization" (1984) Nature 307, 457-460.
Zhou, et al., "Temperature-sensitive neuromuscular transmission in Kv1.1 null mice: role of potassium channels under the myelin sheath in young nerves" (1998) JNeuorsci 18, 7200-7215.
Chen, et al., "A sequence often found in cytoplasmic tails, is required for coated pit mediated internalization of the low density lipoprotein receptor" (1990) J Biol Chem 265, 3116-3123.
Chapman, et al., "Calcium-dependent interaction of the cytoplasmic region of synaptotagmin with membranes. Autonomous function of a single C2-homologous Domain" (1994) J. Biol Chem 269, 5735-5741.
Baldwin, et al., "Association of botulinum neurotoxin serotypes a and B with synaptic vesicle protein complexes" (2007) Biochemistry 46, 3200-3210.
Liu, et al., "A genetic model of substrate deprivation therapy for a glycosphingolipid storage disorder" (1999) J Clin Invest 103, 497-505.
Geppert, et al., "Synaptotagmin 1: a major Ca2+ sensor for transmitter release at a central synapse" (1994) Cell 79, 717-727.
Miesenbock, et al., "Patterns of synaptic activity in neural networks recorded by light emission from synaptolucins" (1997) Proceedings of the National Academy of Sciences of the United States of America 94, 3402-3407.
Malizio, et al., "Purification of Clostridium botulinum Type A Neorotoxin" (2000) Bacterial Toxins Methods and Protocols vol. 145 (ed. O. Holst) 27-39 (Humana Press).
Schiavo, et al., "Neurotoxins affecting neuroexocytosis" (2000) Physiol Rev 80, 717-766.
Simpson "Identification of the major steps in botulinum toxin action" (2004) Annu Rev. Pharmacol Toxicol 44, 167-193.
Arnon et al., "Botulinum toxin as ab iological weapon: medical and public health Management" (2001) JAMA 285, 1059-1070.
Schiavo, et al., "Tetanus and botulinum-B neurotoxins block neurotransmitter release by proteolytic cleavage of synaptobrevin" (1992) Nature 359, 832-835.
Blasi, et al., "Botulinum neurotoxin C1 blocks neurotransmitter release by means of cleaving HPC-1/syntaxin" (1993) Embo J 12, 4821-4828.

(Continued)

*Primary Examiner* — Daniel E Kolker
*Assistant Examiner* — Aditi Dutt
(74) *Attorney, Agent, or Firm* — Quarles & Brady LLP

(57) ABSTRACT

An isolated polypeptide comprising an amino acid sequence selected from amino acids 506-582 of SV2A, wherein position 573 is N and is glycosylated, or amino acids 449-525 of SV2B, wherein position 516 is N and is glycosylated. The present invention also provides an antibody that binds specifically to the polypeptide, an isolated nucleic acid comprising a polynucleotide that encodes the polypeptide; a method for reducing BoNT/E toxicity in an animal; a method for identifying an agent that blocks or inhibits binding between BoNT/E and an SV2A or SV2B protein; a method for monitoring synaptic vesicle endo- or exocytosis, a method for specifically delivering a chemical entity to a cell which has a specific receptor to a BoNT toxin. Also provided are a chimeric toxin for targeting a proteolytic domain of a toxin to a cell, the chimeric toxin comprising a catalytic or proteolytic domain of the BoNT toxin, and a ligand or a fragment thereof for a non-BoNT receptor on the cell; a method for targeting a proteolytic domain of a BoNT toxin to a cell, an isolated non-neuronal cell comprising a BoNT toxin receptor; and a method for screening for an inhibitor of a BoNT toxin.

6 Claims, 13 Drawing Sheets

(56) References Cited

OTHER PUBLICATIONS

Schiavo, et al., "Identification of the nerve terminal targets of botulinum neurotoxin serotypes A,D, and E" (1993) J Biol Chem 268, 23784-23787.
Schiavo, et l., "Botulinum neurotoxin serotype F is a zinc endopeptidase specific for V AMP/synaptobrevin" (1993) J Biol Chem 268, 11516-11519.
Blasi, et al., "Botulinum neurotoxin A selectively cleaves the synaptic protein SNAP-25" (1993) Nature 365, 160-163.
Schiavo, et al., "Botulinum G neurotoxin cleaves VAMP/synaptobrevin at a single AlaAla peptide bond" (1994) J Biol Chem 269, 20213-20216.
Rothman, et al., "Implications of the SNARE hypothesis for intracellular membrane topology and dynamics" (1994) Curr Biol 4, 220-233.
Jahn, et al., "Membrane fusion and exocytosis" (1999) Annu Rev Biochem 68, 863-911.
Jahn, et al., "SNAREs—engines for membrane fusion" (2006) Nat Rev Mol Cell Biol 7, 631-643.
Johnson "Clostridial toxins as therapeutic agents: benefits of nature's most toxic proteins" (1999) Annu Rev Microbiol 53, 551-575.
Aoki "Botulinum toxin: a successful therapeutic protein" (2004) Curr Med Chem 11, 3085-3092.
Dodick, et al., "Botulinum neurotoxin for the treatment of migraine and other primary headache disorders" (2004) Clin Dermatol 22, 76-81.
Montecucco et al., "J. Botulinal neurotoxins: revival of an old killer" (2005) Curr Opin Pharmacol 5, 274-279.
Verderio, et al. "Entering neurons: botulinum toxins and synaptic vesicle recycling" (2006) EMBOR Rep 7, 995-999.
Montecucco "How do tetnus and botulinum toxins bind to neuronal membranes?"(1986) TIBS 314-317.
Kitamura, et al., "Interaction between Clostridium botulinum neurotoxin and gangliosides" (1980) Biochim Biophys Acta 628, 328-335.
Kozaki, et al., "Ganglioside GT1b as a complementary receptor component for Clostridium botulinum neurotoxins" (1998) Microb Pathog 25, 91-99.
Rummel, et al., "The HCC-domain of botulinum neurotoxins A and B exhibits a singular ganglioside binding site displaying serotype specific carbohydrate interaction" (2004) Mol Microbiol 51, 631-643.
Yowler, et al., "Botulinum neurotoxin A changes conformation upon binding to ganglioside GT1b" (2004) Biochemistry 43, 9725-9731.
Yowler, et al., "Botulinum neurotoxin A activity is dependent upon the presence of specific gangliosides in neuroblastoma cells expressing synaptotagmin I" (2002) J Biol Chem 277, 32815-32819.
Chai et al., "Structural basis of cell surface receptor recognition by botulinum neurotoxin B" (2006) Nature 444, 1096-1100.
Dong, et al., "Mechanism of botulinum neurotixin B and G entry into hippocampal neurons" (2007) The Journal of cell biology 179, 1511-1522.
Kitamura, et al., "Gangliosides are the binding substances in neural cells for tetanus and botulinum toxins in mice" (1999) Biochim Biophys Acta 1441, 1-3.
Tsukamoto, et al., "Binding of Clostridium botulinum type C and D neurotoxins to ganglioside and phospholipid. Novel insights into the receptor for clostridial neurotoxins" (2005) J Biol Chem 280, 35164-35171.
Bullens, et al., "Complex gangliosides at the neuromuscular junction are membrane receptors for autoantibodies and botulinum neurotoxin but redundant for normal synaptic function" (2002) JN eurosci 22, 6876-6884.
Rummel, et al., "Identification of the protein receptor binding site of botulinum neurotoxins B and G proves the double-receptor concept" (2007) Proceedings of the National Academy of Sciences of the United States of America 104, 359-364.
Nishiki, et al., "Identification of protein receptor for Clostridium botulinum type B neurotoxin in rat brain synaptosomes" (1994) J Biol Chem 269, 10498-10503.
Nishiki, et al., "The high-affinity binding of Clostridium botulinum type B neurotoxin to Synaptotagmin II associated with gangliosides GT1b/GD1a" (1996) FEBS Lett 378, 253-257.
Dong, et al., "Synaptotagmins I and II mediate entry of botulinum neurotoxin B into Cells" (2003) The Journal of cell biology 162, 1293-1303.
Rummel, et al., "Synaptotagmins I and II act as nerve cell receptors for botulinum neurotoxin G" (2004) J Biol Chem 279, 30865-30870.
Jin, et al., "Botulinum neurotoxin B recognizes its protein receptor with high affinity and specificity" (2006) Nature 444, 1092-1095.
Dong, et al., "SV2 is the protein receptor for botulinum neurotoxin A" (2006) Science 312, 592-596.
Mahrhold, et al., "The synaptic vesicle protein 2C mediates the uptake of botulinum neurotoxin A into phrenic nerves" (2006) FEBS Lett 580, 2011-2014.
Bajjalieh, et al., "SV2, a brain synaptic vesicle protein homologous to bacterial transporters" (1992) Science 257, 1271-1273.
Feany, et al., "The synaptic vesicle protein SV2 is a novel type of transmembrane transporter" (1992) Cell 70, 861-867.
Bajjalieh, et al., "Brain contains two forms of synaptic vesicle protein 2" (1993) Proceedings of the National Academy of Sciences of the United States of America 90, 2150-2154.
Janz, et al., "SV2C is a synaptic vesicle protein with an unusually restricted localization: anatomy of a synaptic vesicle protein family" (1999) Neuroscience 94, 1279-1290.
Buckley, et al., "Identification of a transmembrane glycoprotein specific for secretory vesicles of neural and endocrine cells" (1985) The Journal of cell biology 100, 1284-1294.
Scranton, et al., "The SV2 protein of synaptic vesicles is a keratan sulfate proteoglycan" (1993) Journal of Neurochemistry 61, 29-44.
Sobel "Botulism" (2005) J. Botulism. Clin Infect Dis 41, 1167-1173.
Yule, et al., "Persistence of Clostridium botulinum neurotoxin type E in tissues from selected freshwater fish species: implications to public health" (2006) Journal of Food Protectin 69, 1164-1167.
Lawrence, et al., "Two protein trafficking processes at motor nerve endings unveiled by botulinum neurotoxin E" (2007) The Journal of pharmacology and experimental therapeutics 320, 410-418.
Keller, et al., "Uptake of botulinum neurotoxin into cultured neurons" Biochemistry 43, 526-532.
Crowder, et al., "Abnormal neurotransmission in mice lacking synaptic vesicle protein 2A (SV2A)" (1999) Proceedings of the National Academy of Sciences of the United States of America 96, 15268-15273.
Janz, et al., "SV2A and SV2B function as redundant Ca2+ regulators in neurotransmitter release" (1999) Neuron 24, 1003-1016.
Bajjalieh, et al., "Differential expression of synaptic vesicle protein 2 (SV2) isoforms" (1994) J Neurosci 14, 5223-5235.
Verderio, et al., "Traffic of botulinum toxins A and E in excitatory and inhibitory Neurons" (2007) Traffic (Copenhagen, Denmark) 8, 142-153.

* cited by examiner

Figure 6

Amino Acid Sequences SV2A Proteins

Human SV2A

```
  1 MEEGFRDRAA FIRGAKDIAK EVKKHAAKKV VKGLDRVQDE YSRRSYSRFE EEDDDDDFPA
 61 PSDGYYRGEG TQDEEEGGAS SDATEGHDED DEIYEGEYQG IPRAESGGKG ERMADGAPLA
121 GVRGGLSDGE GPPGGRGEAQ RRKEREELAQ QYEAILRECG HGRFQWTLYF VLGLALMADG
181 VEVFVVGFVL PSAEKDMCLS DSNKGMLGLI VYLGMMVGAF LWGGLADRLG RRQCLLISLS
241 VNSVFAFFSS FVQGYGTFLF CRLLSGVGIG GSIPIVFSYF SEFLAQEKRG EHLSWLCMFW
301 MIGGVYAAAM AWAIIPHYGW SFQMGSAYQF HSWRVFVLVC AFPSVFAIGA LTTQPESPRF
361 FLENGKHDEA WMVLKQVHDT NMRAKGHPER VFSVTHIKTI HQEDELIEIQ SDTGTWYQRW
421 GVRALSLGGQ VWGNFLSCFG PEYRRITLMM MGVWFTMSFS YYGLTVWFPD MIRHLQAVDY
481 ASRTKVFPGE RVEHVTFNFT ░░░░░░░░░░ ░░░░░░░░░░ ░░░░░░░░░░ ░░░░░░░░░░
    ░░░░░░░░░░ ░░░░░░░░░░ ░░░░░░░░░░ ░░░░░░░░░░ ░░CPLDVTGT GEGAYMVYFV
601 SFLGTLAVLP GNIVSALLMD KIGRLRMLAG SSVMSCVSCF FLSFGNSESA MIALLCLFGG
661 VSIASWNALD VLTVELYPSD KRTTAFGFLN ALCKLAAVLG ISIFTSFVGI TKAAPILFAS
721 AALALGSSLA LKLPETRGQV LQ
```

Mouse SV2A

```
  1 MEEGFRDRAA FIRGAKDIAK EVKKHAAKKV VKGLDRVQDE YSRRSYSRFE EEDDDDDFPA
 61 PADGYYRGEG AQDEEEGGAS SDATEGHDED DEIYEGEYQG IPRAESGGKG ERMADGAPLA
121 GVRGGLSDGE GPPGGRGEAQ RRKDREELAQ QYETILRECG HGRFQWTLYF VLGLALMADG
181 VEVFVVGFVL PSAEKDMCLS DSNKGMLGLI VYLGMMVGAF LWGGLADRLG RRQCLLISLS
241 VNSVFAFFSS FVQGYGTFLF CRLLSGVGIG GSIPIVFSYF SEFLAQEKRG EHLSWLCMFW
301 MIGGVYAAAM AWAIIPHYGW SFQMGSAYQF HSWRVFVLVC AFPSVFAIGA LTTQPESPRF
361 FLENGKHDEA WMVLKQVHDT NMRAKGHPER VFSVTHIKTI HQEDELIEIQ SDTGTWYQRW
421 GVRALSLGGQ VWGNFLSCFS PEYRRITLMM MGVWFTMSFS YYGLTVWFPD MIRHLQAVDY
481 AARTKVFPGE RVEHVTFNFT ░░░░░░░░░░ ░░░░░░░░░░ ░░░░░░░░░░ ░░░░░░░░░░
    ░░░░░░░░░░ ░░░░░░░░░░ ░░░░░░░░░░ ░░░░░░░░░░ ░░CPLDVTGT GEGAYMVYFV
601 SFLGTLAVLP GNIVSALLMD KIGRLRMLAG SSVLSCVSCF FLSFGNSESA MIALLCLFGG
661 VSIASWNALD VLTVELYPSD KRTTAFGFLN ALCKLAAVLG ISIFTSFVGI TKAAPILFAS
721 AALALGSSLA LKLPETRGQV LQ
```

RAT SV2A

```
  1 MEEGFRDRAA FIRGAKDIAK EVKKHAAKKV VKGLDRVQDE YSRRSYSRFE EEDDDDDFPA
 61 PADGYYRGEG AQDEEEGGAS SDATEGHDED DEIYEGEYQG IPRAESGGKG ERMADGAPLA
121 GVRGGLSDGE GPPGGRGEAQ RRKDREELAQ QYETILRECG HGRFQWTLYF VLGLALMADG
181 VEVFVVGFVL PSAEKDMCLS DSNKGMLGLI VYLGMMVGAF LWGGLADRLG RRQCLLISLS
241 VNSVFAFFSS FVQGYGTFLF CRLLSGVGIG GSIPIVFSYF SEFLAQEKRG EHLSWLCMFW
301 MIGGVYAAAM AWAIIPHYGW SFQMGSAYQF HSWRVFVLVC AFPSVFAIGA LTTQPESPRF
361 FLENGKHDEA WMVLKQVHDT NMRAKGHPER VFSVTHIKTI HQEDELIEIQ SDTGTWYQRW
421 GVRALSLGGQ VWGNFLSCFS PEYRRITLMM MGVWFTMSFS YYGLTVWFPD MIRHLQAVDY
481 AARTKVFPGE RVEHVTFNFT ░░░░░░░░░░ ░░░░░░░░░░ ░░░░░░░░░░ ░░░░░░░░░░
    ░░░░░░░░░░ ░░░░░░░░░░ ░░░░░░░░░░ ░░░░░░░░░░ ░░CPLDVTGT GEGAYMVYFV
601 SFLGTLAVLP GNIVSALLMD KIGRLRMLAG SSVLSCVSCF FLSFGNSESA MIALLCLFGG
661 VSIASWNALD VLTVELYPSD KRTTAFGFLN ALCKLAAVLG ISIFTSFVGI TKAAPILFAS
721 AALALGSSLA LKLPETRGQV LQ
```

Figure 8A

Amino Acid Sequences SV2B Proteins

SV2B HUMAN

```
  1 MDDYKYQDNY GGYAPSDGYY RGNESNPEED AQSDVTEGHD EEDEIYEGEY QGIPHPDDVK
 61 AKQAKMAPSR MDSLRGQTDL MAERLEDEEQ LAHQYETIMD ECGHGRFQWI LFFVLGLALM
121 ADGVEVFVVS FALPSAEKDM CLSSSKKGML GMIVYLGMMA GAFILGGLAD KLGRKRVLSM
181 SLAVNASFAS LSSFVQGYGA FLFCRLISGI GIGGALPIVF AYFSEFLSRE KRGEHLSWLG
241 IFWMTGGLYA SAMAWSIIPH YGWGFSMGTN YHFHSWRVFV IVCALPCTVS MVALKFMPES
301 PRFLLEMGKH DEAWMILKQV HDTNMPAKGT PEKVFTVSNI KTPKQMDEFI EIQSSTGTWY
361 QRWLVRFKTI FKQVWDNALY CVMGPYRMNT LILAVVWFAM AFSYYGLTV
421
481                                                                L
541 VSFLGSLSVL PGNIISALLM DRIGRLKMIG GSMLISAVCC FFLFFGNSES AMIGWQCLFC
601 GTSIAAWNAL DVITVELYPT NQRATAFGIL NGLCKFGAIL GNTIFASFVG ITKVVPILLA
661 AASLVGGGLI ALRLPETREQ VLM
```

SV2B MOUSE

```
  1 MDDYRYRDNY EGYAPSDGYY RSNEQNQEED AQSDVTEGHD EEDEIYEGEY QGIPHPDDVK
 61 SKQTKMAPSR ADGLGGQADL MAERMEDEEE LAHQYETIID ECGHGRFQWT LFFVLGLALM
121 ADGVEIFVVS FALPSAEKDM CLSSSKKGML GLIVYLGMMA GAFILGGLAD KLGRKKVLSM
181 SLAINASFAS LSSFVQGYGA FLFCRLISGI GIGGSLPIVF AYFSEFLSRE KRGEHLSWLG
241 IFWMTGGIYA SAMAWSIIPH YGWGFSMGTN YHFHSWRVFV IVCALPATVS MVALKFMPES
301 PRFLLEMGKH DEAWMILKQV HDTNMRAKGT PEKVFTVSHI KTPKQMDEFI EIQSSTGTWY
361 QRWLVRFMTI FKQVWDNALY CVMGPYRMNT LILAVVWFTM
421
481                                                        EEDNDFLIYL
541 VSFLGSLSVL PGNIISALLM DRIGRLKMIG GSMLISAVCC FFLFFGNSES AMIGWQCLFC
601 GTSIAAWNAL DVITVELYPT NQRATAFGIL NGLCKFGAIL GNTIFASFVG ITKVVPILLA
661 AASLVGGGLI ALRLPETREQ VLM
```

RAT SV2B

```
  1 MDDYRYRDNY EGYAPNDGYY RGNEQNPEED AQSDVTEGHD EEDEIYEGEY QGIPHPDDVK
 61 SKQTKMAPSR ADGLPGQADL MAERMEDEEQ LAHQYETIID ECGHGRFQWT LFFVLVLALM
121 ADGVEVFVVS FALPSAEKDM CLSSSKKGML GLIVYLGMMA GAFILGGLAD KLGRKKVLSM
181 SLAINASFAS LSSFVQGYGA FLFCRLISGI GIGGSLPIVF AYFSEFLSRE KRGEHLSWLG
241 IFWMTGGIYA SAMAWSIIPH YGWGFSMGTN YHFHSWRVFV IVCALPATVS MVALKFMPES
301 PRFLLEMGKH DEAWMILKQV HDTNMRAKGT PEKVFTVSHI KTPKQMDEFI EIQSSTGTWY
361 QRWLVRFMTI FKQVWDNALY CVMGPYRMNT LILAVVWFTM ALSYYGLTV
421
481                                                        EEDNDFLIYL
541 VSFLGSLSVL PGNIISALLM DRIGRLKMIG GSMLISAVCC FFLFFGNSES AMIGWQCLFC
601 GTSIAAWNAL DVITVELYPT NQRATAFGIL NGLCKLGAIL GNTIFASFVG ITKVVPILLA
661 AASLVGGGLV ALRLPETREQ VLM
```

Highlighted portion is 410-539, the L4 domain

Figure 8B

SEQUENCE LISTING

```
<160> NUMBER OF SEQ ID NOS: 9

<210> SEQ ID NO 1
<211> LENGTH: 82
<212> TYPE: PRT
<213> ORGANISM: Mus musculus
<220> FEATURE:
<221> NAME/KEY: misc_feature
<223> OTHER INFORMATION: MOUSE SV2A LUMINAL

<400> SEQUENCE: 1

Thr Phe Asn Phe Thr His Arg Gly Gly Gln Tyr Phe Asn Asp Lys Phe
1               5                   10                  15

Ile Gly Leu Arg Leu Lys Ser Val Ser Phe Glu Asp Ser Leu Phe Glu
            20                  25                  30

Glu Cys Tyr Phe Glu Asp Val Thr Ser Ser Asn Thr Phe Phe Arg Asn
        35                  40                  45

Cys Thr Phe Ile Asn Thr Val Phe Tyr Asn Thr Asp Leu Phe Glu Tyr
    50                  55                  60

Lys Phe Val Asn Ser Arg Leu Val Asn Ser Thr Phe Leu His Asn Lys
65                  70                  75                  80

Glu Gly

<210> SEQ ID NO 2
<211> LENGTH: 82
<212> TYPE: PRT
<213> ORGANISM: Mus musculus
<220> FEATURE:
<221> NAME/KEY: misc_feature
<223> OTHER INFORMATION: MOUSE SV2B LUMINAL

<400> SEQUENCE: 2

Thr Ile Asn Phe Thr His Gln His Gly Lys Leu Val Asn Asp Lys Phe
1               5                   10                  15

Ile Lys Met Tyr Phe Lys His Val Leu Phe Glu Asp Thr Phe Phe Asp
            20                  25                  30
```

Lys Cys Tyr Phe Glu Asp Val Thr Ser Thr Asp Tyr Phe Lys Asn
                35                  40                  45

Cys Thr Ile Glu Ser Thr Thr Phe Tyr Asn Thr Asp Leu Tyr Lys His
 50                  55                  60

Lys Phe Ile Asn Cys Arg Phe Ile Asn Ser Thr Phe Leu Glu Gln Lys
 65                  70                  75                  80

Glu Gly

<210> SEQ ID NO 3
<211> LENGTH: 82
<212> TYPE: PRT
<213> ORGANISM: Mus musculus
<220> FEATURE:
<221> NAME/KEY: misc_feature
<223> OTHER INFORMATION: MOUSE SV2C LUMINAL

<400> SEQUENCE: 3

Ser Ile Asn Phe Thr His Thr Gly Met Glu Tyr Glu Asn Gly Arg Phe
1               5                   10                  15

Leu Gly Val Lys Phe Lys Ser Val Thr Phe Lys Asp Ser Val Phe Lys
                20                  25                  30

Ser Cys Thr Phe Asp Asp Val Thr Ser Val Asn Thr Tyr Phe Lys Asn
                35                  40                  45

Cys Thr Phe Ile Asp Thr Leu Phe Asp Asn Thr Asp Phe Glu Pro Tyr
 50                  55                  60

Lys Phe Ile Asp Ser Glu Phe Gln Asn Cys Ser Phe Leu His Asn Lys
 65                  70                  75                  80

Thr Gly

<210> SEQ ID NO 4
<211> LENGTH: 742
<212> TYPE: PRT
<213> ORGANISM: Homo sapiens
<220> FEATURE:
<221> NAME/KEY: misc_feature
<223> OTHER INFORMATION: HUMAN SV2A

<400> SEQUENCE: 4

Met Glu Glu Gly Phe Arg Asp Arg Ala Ala Phe Ile Arg Gly Ala Lys
1               5                   10                  15

Asp Ile Ala Lys Glu Val Lys Lys His Ala Ala Lys Lys Val Val Lys
                20                  25                  30

Gly Leu Asp Arg Val Gln Asp Glu Tyr Ser Arg Arg Ser Tyr Ser Arg
                35                  40                  45

Phe Glu Glu Glu Asp Asp Asp Asp Phe Pro Ala Pro Ser Asp Gly
 50                  55                  60

Tyr Tyr Arg Gly Glu Gly Thr Gln Asp Glu Glu Gly Gly Ala Ser
 65                  70                  75                  80

Ser Asp Ala Thr Glu Gly His Asp Glu Asp Asp Glu Ile Tyr Glu Gly
                85                  90                  95

Glu Tyr Gln Gly Ile Pro Arg Ala Glu Ser Gly Gly Lys Gly Glu Arg
                100                 105                 110

Met Ala Asp Gly Ala Pro Leu Ala Gly Val Arg Gly Gly Leu Ser Asp
                115                 120                 125

Gly Glu Gly Pro Pro Gly Gly Arg Gly Glu Ala Gln Arg Arg Lys Glu
                130                 135                 140

Arg Glu Glu Leu Ala Gln Gln Tyr Glu Ala Ile Leu Arg Glu Cys Gly
145                 150                 155                 160

-continued

His Gly Arg Phe Gln Trp Thr Leu Tyr Phe Val Leu Gly Leu Ala Leu
              165                 170                 175

Met Ala Asp Gly Val Glu Val Phe Val Val Gly Phe Val Leu Pro Ser
              180                 185                 190

Ala Glu Lys Asp Met Cys Leu Ser Asp Ser Asn Lys Gly Met Leu Gly
              195                 200                 205

Leu Ile Val Tyr Leu Gly Met Met Val Gly Ala Phe Leu Trp Gly Gly
              210                 215                 220

Leu Ala Asp Arg Leu Gly Arg Arg Gln Cys Leu Leu Ile Ser Leu Ser
225                 230                 235                 240

Val Asn Ser Val Phe Ala Phe Phe Ser Ser Phe Val Gln Gly Tyr Gly
              245                 250                 255

Thr Phe Leu Phe Cys Arg Leu Leu Ser Gly Val Gly Ile Gly Gly Ser
              260                 265                 270

Ile Pro Ile Val Phe Ser Tyr Phe Ser Glu Phe Leu Ala Gln Glu Lys
              275                 280                 285

Arg Gly Glu His Leu Ser Trp Leu Cys Met Phe Trp Met Ile Gly Gly
              290                 295                 300

Val Tyr Ala Ala Met Ala Trp Ala Ile Ile Pro His Tyr Gly Trp
305                 310                 315                 320

Ser Phe Gln Met Gly Ser Ala Tyr Gln Phe His Ser Trp Arg Val Phe
              325                 330                 335

Val Leu Val Cys Ala Phe Pro Ser Val Phe Ala Ile Gly Ala Leu Thr
              340                 345                 350

Thr Gln Pro Glu Ser Pro Arg Phe Phe Leu Glu Asn Gly Lys His Asp
              355                 360                 365

Glu Ala Trp Met Val Leu Lys Gln Val His Asp Thr Asn Met Arg Ala
370                 375                 380

Lys Gly His Pro Glu Arg Val Phe Ser Val Thr His Ile Lys Thr Ile
385                 390                 395                 400

His Gln Glu Asp Glu Leu Ile Glu Ile Gln Ser Asp Thr Gly Thr Trp
              405                 410                 415

Tyr Gln Arg Trp Gly Val Arg Ala Leu Ser Leu Gly Gly Gln Val Trp
              420                 425                 430

Gly Asn Phe Leu Ser Cys Phe Gly Pro Glu Tyr Arg Arg Ile Thr Leu
              435                 440                 445

Met Met Met Gly Val Trp Phe Thr Met Ser Phe Ser Tyr Tyr Gly Leu
              450                 455                 460

Thr Val Trp Phe Pro Asp Met Ile Arg His Leu Gln Ala Val Asp Tyr
465                 470                 475                 480

Ala Ser Arg Thr Lys Val Phe Pro Gly Glu Arg Val Glu His Val Thr
              485                 490                 495

Phe Asn Phe Thr Leu Glu Asn Gln Ile His Arg Gly Gly Gln Tyr Phe
              500                 505                 510

Asn Asp Lys Phe Ile Gly Leu Arg Leu Lys Ser Val Ser Phe Glu Asp
              515                 520                 525

Ser Leu Phe Glu Glu Cys Tyr Phe Glu Asp Val Thr Ser Ser Asn Thr
              530                 535                 540

Phe Phe Arg Asn Cys Thr Phe Ile Asn Thr Val Phe Tyr Asn Thr Asp
545                 550                 555                 560

Leu Phe Glu Tyr Lys Phe Val Asn Ser Arg Leu Ile Asn Ser Thr Phe
              565                 570                 575

```
Leu His Asn Lys Glu Gly Cys Pro Leu Asp Val Thr Gly Thr Gly Glu
                580                 585                 590

Gly Ala Tyr Met Val Tyr Phe Val Ser Phe Leu Gly Thr Leu Ala Val
            595                 600                 605

Leu Pro Gly Asn Ile Val Ser Ala Leu Leu Met Asp Lys Ile Gly Arg
        610                 615                 620

Leu Arg Met Leu Ala Gly Ser Ser Val Met Ser Cys Val Ser Cys Phe
625                 630                 635                 640

Phe Leu Ser Phe Gly Asn Ser Glu Ser Ala Met Ile Ala Leu Leu Cys
                645                 650                 655

Leu Phe Gly Gly Val Ser Ile Ala Ser Trp Asn Ala Leu Asp Val Leu
            660                 665                 670

Thr Val Glu Leu Tyr Pro Ser Asp Lys Arg Thr Thr Ala Phe Gly Phe
        675                 680                 685

Leu Asn Ala Leu Cys Lys Leu Ala Ala Val Leu Gly Ile Ser Ile Phe
690                 695                 700

Thr Ser Phe Val Gly Ile Thr Lys Ala Ala Pro Ile Leu Phe Ala Ser
705                 710                 715                 720

Ala Ala Leu Ala Leu Gly Ser Ser Leu Ala Leu Lys Leu Pro Glu Thr
                725                 730                 735

Arg Gly Gln Val Leu Gln
            740

<210> SEQ ID NO 5
<211> LENGTH: 742
<212> TYPE: PRT
<213> ORGANISM: Mus musculus
<220> FEATURE:
<221> NAME/KEY: misc_feature
<223> OTHER INFORMATION: MOUSE SV2B

<400> SEQUENCE: 5

Met Glu Glu Gly Phe Arg Asp Arg Ala Ala Phe Ile Arg Gly Ala Lys
1               5                   10                  15

Asp Ile Ala Lys Glu Val Lys Lys His Ala Ala Lys Lys Val Val Lys
            20                  25                  30

Gly Leu Asp Arg Val Gln Asp Glu Tyr Ser Arg Arg Ser Tyr Ser Arg
        35                  40                  45

Phe Glu Glu Glu Asp Asp Asp Asp Phe Pro Ala Pro Ala Asp Gly
    50                  55                  60

Tyr Tyr Arg Gly Glu Gly Ala Gln Asp Glu Glu Gly Gly Ala Ser
65                  70                  75                  80

Ser Asp Ala Thr Glu Gly His Asp Glu Asp Glu Ile Tyr Glu Gly
                85                  90                  95

Glu Tyr Gln Gly Ile Pro Arg Ala Glu Ser Gly Gly Lys Gly Glu Arg
            100                 105                 110

Met Ala Asp Gly Ala Pro Leu Ala Gly Val Arg Gly Gly Leu Ser Asp
        115                 120                 125

Gly Glu Gly Pro Pro Gly Gly Arg Gly Glu Ala Gln Arg Arg Lys Asp
130                 135                 140

Arg Glu Glu Leu Ala Gln Gln Tyr Glu Thr Ile Leu Arg Glu Cys Gly
145                 150                 155                 160

His Gly Arg Phe Gln Trp Thr Leu Tyr Phe Val Leu Gly Leu Ala Leu
                165                 170                 175

Met Ala Asp Gly Val Glu Val Phe Val Val Gly Phe Val Leu Pro Ser
            180                 185                 190
```

-continued

```
Ala Glu Lys Asp Met Cys Leu Ser Asp Ser Asn Lys Gly Met Leu Gly
            195                 200                 205

Leu Ile Val Tyr Leu Gly Met Met Val Gly Ala Phe Leu Trp Gly Gly
        210                 215                 220

Leu Ala Asp Arg Leu Gly Arg Arg Gln Cys Leu Leu Ile Ser Leu Ser
225                 230                 235                 240

Val Asn Ser Val Phe Ala Phe Phe Ser Ser Phe Val Gln Gly Tyr Gly
                245                 250                 255

Thr Phe Leu Phe Cys Arg Leu Leu Ser Gly Val Gly Ile Gly Gly Ser
            260                 265                 270

Ile Pro Ile Val Phe Ser Tyr Phe Ser Glu Phe Leu Ala Gln Glu Lys
        275                 280                 285

Arg Gly Glu His Leu Ser Trp Leu Cys Met Phe Trp Met Ile Gly Gly
            290                 295                 300

Val Tyr Ala Ala Ala Met Ala Trp Ala Ile Ile Pro His Tyr Gly Trp
305                 310                 315                 320

Ser Phe Gln Met Gly Ser Ala Tyr Gln Phe His Ser Trp Arg Val Phe
                325                 330                 335

Val Leu Val Cys Ala Phe Pro Ser Val Phe Ala Ile Gly Ala Leu Thr
            340                 345                 350

Thr Gln Pro Glu Ser Pro Arg Phe Phe Leu Glu Asn Gly Lys His Asp
        355                 360                 365

Glu Ala Trp Met Val Leu Lys Gln Val His Asp Thr Asn Met Arg Ala
        370                 375                 380

Lys Gly His Pro Glu Arg Val Phe Ser Val Thr His Ile Lys Thr Ile
385                 390                 395                 400

His Gln Glu Asp Glu Leu Ile Glu Ile Gln Ser Asp Thr Gly Thr Trp
                405                 410                 415

Tyr Gln Arg Trp Gly Val Arg Ala Leu Ser Leu Gly Gly Gln Val Trp
            420                 425                 430

Gly Asn Phe Leu Ser Cys Phe Ser Pro Glu Tyr Arg Arg Ile Thr Leu
        435                 440                 445

Met Met Met Gly Val Trp Phe Thr Met Ser Phe Ser Tyr Tyr Gly Leu
        450                 455                 460

Thr Val Trp Phe Pro Asp Met Ile Arg His Leu Gln Ala Val Asp Tyr
465                 470                 475                 480

Ala Ala Arg Thr Lys Val Phe Pro Gly Glu Arg Val Glu His Val Thr
                485                 490                 495

Phe Asn Phe Thr Leu Glu Asn Gln Ile His Arg Gly Gly Gln Tyr Phe
            500                 505                 510

Asn Asp Lys Phe Ile Gly Leu Arg Leu Lys Ser Val Ser Phe Glu Asp
        515                 520                 525

Ser Leu Phe Glu Glu Cys Tyr Phe Glu Asp Val Thr Ser Ser Asn Thr
        530                 535                 540

Phe Phe Arg Asn Cys Thr Phe Ile Asn Thr Val Phe Tyr Asn Thr Asp
545                 550                 555                 560

Leu Phe Glu Tyr Lys Phe Val Asn Ser Arg Leu Val Asn Ser Thr Phe
                565                 570                 575

Leu His Asn Lys Glu Gly Cys Pro Leu Asp Val Thr Gly Thr Gly Glu
            580                 585                 590

Gly Ala Tyr Met Val Tyr Phe Val Ser Phe Leu Gly Thr Leu Ala Val
        595                 600                 605
```

```
Leu Pro Gly Asn Ile Val Ser Ala Leu Leu Met Asp Lys Ile Gly Arg
        610                 615                 620

Leu Arg Met Leu Ala Gly Ser Ser Val Leu Ser Cys Val Ser Cys Phe
625                 630                 635                 640

Phe Leu Ser Phe Gly Asn Ser Glu Ser Ala Met Ile Ala Leu Leu Cys
            645                 650                 655

Leu Phe Gly Gly Val Ser Ile Ala Ser Trp Asn Ala Leu Asp Val Leu
            660                 665                 670

Thr Val Glu Leu Tyr Pro Ser Asp Lys Arg Thr Thr Ala Phe Gly Phe
        675                 680                 685

Leu Asn Ala Leu Cys Lys Leu Ala Ala Val Leu Gly Ile Ser Ile Phe
    690                 695                 700

Thr Ser Phe Val Gly Ile Thr Lys Ala Ala Pro Ile Leu Phe Ala Ser
705                 710                 715                 720

Ala Ala Leu Ala Leu Gly Ser Ser Leu Ala Leu Lys Leu Pro Glu Thr
            725                 730                 735

Arg Gly Gln Val Leu Gln
            740

<210> SEQ ID NO 6
<211> LENGTH: 742
<212> TYPE: PRT
<213> ORGANISM: Rattus norvegicus
<220> FEATURE:
<221> NAME/KEY: misc_feature
<223> OTHER INFORMATION: RAT SV2A

<400> SEQUENCE: 6

Met Glu Glu Gly Phe Arg Asp Arg Ala Ala Phe Ile Arg Gly Ala Lys
1               5                   10                  15

Asp Ile Ala Lys Glu Val Lys Lys His Ala Ala Lys Lys Val Val Lys
            20                  25                  30

Gly Leu Asp Arg Val Gln Asp Glu Tyr Ser Arg Arg Ser Tyr Ser Arg
        35                  40                  45

Phe Glu Glu Glu Glu Asp Asp Asp Phe Pro Ala Pro Ala Asp Gly
50                  55                  60

Tyr Tyr Arg Gly Glu Gly Ala Gln Asp Glu Glu Gly Gly Ala Ser
65                  70                  75                  80

Ser Asp Ala Thr Glu Gly His Asp Glu Asp Asp Glu Ile Tyr Glu Gly
            85                  90                  95

Glu Tyr Gln Gly Ile Pro Arg Ala Glu Ser Gly Gly Lys Gly Glu Arg
        100                 105                 110

Met Ala Asp Gly Ala Pro Leu Ala Gly Val Arg Gly Gly Leu Ser Asp
    115                 120                 125

Gly Glu Gly Pro Pro Gly Gly Arg Gly Glu Ala Gln Arg Arg Lys Asp
130                 135                 140

Arg Glu Glu Leu Ala Gln Gln Tyr Glu Thr Ile Leu Arg Glu Cys Gly
145                 150                 155                 160

His Gly Arg Phe Gln Trp Thr Leu Tyr Phe Val Leu Gly Leu Ala Leu
            165                 170                 175

Met Ala Asp Gly Val Glu Val Phe Val Val Gly Phe Val Leu Pro Ser
        180                 185                 190

Ala Glu Lys Asp Met Cys Leu Ser Asp Ser Asn Lys Gly Met Leu Gly
    195                 200                 205

Leu Ile Val Tyr Leu Gly Met Met Val Gly Ala Phe Leu Trp Gly Gly
210                 215                 220
```

```
Leu Ala Asp Arg Leu Gly Arg Arg Gln Cys Leu Leu Ile Ser Leu Ser
225                 230                 235                 240

Val Asn Ser Val Phe Ala Phe Phe Ser Ser Phe Val Gln Gly Tyr Gly
                245                 250                 255

Thr Phe Leu Phe Cys Arg Leu Leu Ser Gly Val Gly Ile Gly Gly Ser
            260                 265                 270

Ile Pro Ile Val Phe Ser Tyr Phe Ser Glu Phe Leu Ala Gln Glu Lys
        275                 280                 285

Arg Gly Glu His Leu Ser Trp Leu Cys Met Phe Trp Met Ile Gly Gly
    290                 295                 300

Val Tyr Ala Ala Ala Met Ala Trp Ala Ile Ile Pro His Tyr Gly Trp
305                 310                 315                 320

Ser Phe Gln Met Gly Ser Ala Tyr Gln Phe His Ser Trp Arg Val Phe
                325                 330                 335

Val Leu Val Cys Ala Phe Pro Ser Val Phe Ala Ile Gly Ala Leu Thr
            340                 345                 350

Thr Gln Pro Glu Ser Pro Arg Phe Phe Leu Glu Asn Gly Lys His Asp
        355                 360                 365

Glu Ala Trp Met Val Leu Lys Gln Val His Asp Thr Asn Met Arg Ala
370                 375                 380

Lys Gly His Pro Glu Arg Val Phe Ser Val Thr His Ile Lys Thr Ile
385                 390                 395                 400

His Gln Glu Asp Glu Leu Ile Glu Ile Gln Ser Asp Thr Gly Thr Trp
                405                 410                 415

Tyr Gln Arg Trp Gly Val Arg Ala Leu Ser Leu Gly Gly Gln Val Trp
            420                 425                 430

Gly Asn Phe Leu Ser Cys Phe Ser Pro Glu Tyr Arg Arg Ile Thr Leu
        435                 440                 445

Met Met Met Gly Val Trp Phe Thr Met Ser Phe Ser Tyr Tyr Gly Leu
450                 455                 460

Thr Val Trp Phe Pro Asp Met Ile Arg His Leu Gln Ala Val Asp Tyr
465                 470                 475                 480

Ala Ala Arg Thr Lys Val Phe Pro Gly Glu Arg Val Glu His Val Thr
                485                 490                 495

Phe Asn Phe Thr Leu Glu Asn Gln Ile His Arg Gly Gly Gln Tyr Phe
            500                 505                 510

Asn Asp Lys Phe Ile Gly Leu Arg Leu Lys Ser Val Ser Phe Glu Asp
        515                 520                 525

Ser Leu Phe Glu Glu Cys Tyr Phe Glu Asp Val Thr Ser Ser Asn Thr
530                 535                 540

Phe Phe Arg Asn Cys Thr Phe Ile Asn Thr Val Phe Tyr Asn Thr Asp
545                 550                 555                 560

Leu Phe Glu Tyr Lys Phe Val Asn Ser Arg Leu Val Asn Ser Thr Phe
                565                 570                 575

Leu His Asn Lys Glu Gly Cys Pro Leu Asp Val Thr Gly Thr Gly Glu
            580                 585                 590

Gly Ala Tyr Met Val Tyr Phe Val Ser Phe Leu Gly Thr Leu Ala Val
        595                 600                 605

Leu Pro Gly Asn Ile Val Ser Ala Leu Leu Met Asp Lys Ile Gly Arg
    610                 615                 620

Leu Arg Met Leu Ala Gly Ser Ser Val Leu Ser Cys Val Ser Cys Phe
625                 630                 635                 640
```

```
Phe Leu Ser Phe Gly Asn Ser Glu Ser Ala Met Ile Ala Leu Leu Cys
                    645                 650                 655

Leu Phe Gly Gly Val Ser Ile Ala Ser Trp Asn Ala Leu Asp Val Leu
            660                 665                 670

Thr Val Glu Leu Tyr Pro Ser Asp Lys Arg Thr Thr Ala Phe Gly Phe
            675                 680                 685

Leu Asn Ala Leu Cys Lys Leu Ala Ala Val Leu Gly Ile Ser Ile Phe
            690                 695                 700

Thr Ser Phe Val Gly Ile Thr Lys Ala Ala Pro Ile Leu Phe Ala Ser
705                 710                 715                 720

Ala Ala Leu Ala Leu Gly Ser Ser Leu Ala Leu Lys Leu Pro Glu Thr
            725                 730                 735

Arg Gly Gln Val Leu Gln
            740

<210> SEQ ID NO 7
<211> LENGTH: 683
<212> TYPE: PRT
<213> ORGANISM: Homo sapiens

<400> SEQUENCE: 7

Met Asp Asp Tyr Lys Tyr Gln Asp Asn Tyr Gly Gly Tyr Ala Pro Ser
1               5                   10                  15

Asp Gly Tyr Tyr Arg Gly Asn Glu Ser Asn Pro Glu Glu Asp Ala Gln
            20                  25                  30

Ser Asp Val Thr Glu Gly His Asp Glu Glu Asp Glu Ile Tyr Glu Gly
        35                  40                  45

Glu Tyr Gln Gly Ile Pro His Pro Asp Asp Val Lys Ala Lys Gln Ala
    50                  55                  60

Lys Met Ala Pro Ser Arg Met Asp Ser Leu Arg Gly Gln Thr Asp Leu
65                  70                  75                  80

Met Ala Glu Arg Leu Glu Asp Glu Gln Leu Ala His Gln Tyr Glu
                85                  90                  95

Thr Ile Met Asp Glu Cys Gly His Gly Arg Phe Gln Trp Ile Leu Phe
                100                 105                 110

Phe Val Leu Gly Leu Ala Leu Met Ala Asp Gly Val Glu Val Phe Val
            115                 120                 125

Val Ser Phe Ala Leu Pro Ser Ala Glu Lys Asp Met Cys Leu Ser Ser
        130                 135                 140

Ser Lys Lys Gly Met Leu Gly Met Ile Val Tyr Leu Gly Met Met Ala
145                 150                 155                 160

Gly Ala Phe Ile Leu Gly Gly Leu Ala Asp Lys Leu Gly Arg Lys Arg
                165                 170                 175

Val Leu Ser Met Ser Leu Ala Val Asn Ala Ser Phe Ala Ser Leu Ser
            180                 185                 190

Ser Phe Val Gln Gly Tyr Gly Ala Phe Leu Phe Cys Arg Leu Ile Ser
        195                 200                 205

Gly Ile Gly Ile Gly Gly Ala Leu Pro Ile Val Phe Ala Tyr Phe Ser
    210                 215                 220

Glu Phe Leu Ser Arg Glu Lys Arg Gly Glu His Leu Ser Trp Leu Gly
225                 230                 235                 240

Ile Phe Trp Met Thr Gly Gly Leu Tyr Ala Ser Ala Met Ala Trp Ser
                245                 250                 255

Ile Ile Pro His Tyr Gly Trp Gly Phe Ser Met Gly Thr Asn Tyr His
            260                 265                 270
```

```
Phe His Ser Trp Arg Val Phe Ile Val Cys Ala Leu Pro Cys Thr
        275                 280                 285
Val Ser Met Val Ala Leu Lys Phe Met Pro Glu Ser Pro Arg Phe Leu
290                 295                 300
Leu Glu Met Gly Lys His Asp Glu Ala Trp Met Ile Leu Lys Gln Val
305                 310                 315                 320
His Asp Thr Asn Met Arg Ala Lys Gly Thr Pro Glu Lys Val Phe Thr
                    325                 330                 335
Val Ser Asn Ile Lys Thr Pro Lys Gln Met Asp Glu Phe Ile Glu Ile
                    340                 345                 350
Gln Ser Ser Thr Gly Thr Trp Tyr Gln Arg Trp Leu Val Arg Phe Lys
                355                 360                 365
Thr Ile Phe Lys Gln Val Trp Asp Asn Ala Leu Tyr Cys Val Met Gly
            370                 375                 380
Pro Tyr Arg Met Asn Thr Leu Ile Leu Ala Val Val Trp Phe Ala Met
385                 390                 395                 400
Ala Phe Ser Tyr Tyr Gly Leu Thr Val Trp Phe Pro Asp Met Ile Arg
                405                 410                 415
Tyr Phe Gln Asp Glu Glu Tyr Lys Ser Lys Met Lys Val Phe Phe Gly
                420                 425                 430
Glu His Val Tyr Gly Ala Thr Ile Asn Phe Thr Met Glu Asn Gln Ile
            435                 440                 445
His Gln His Gly Lys Leu Val Asn Asp Lys Phe Thr Arg Met Tyr Phe
450                 455                 460
Lys His Val Leu Phe Glu Asp Thr Phe Phe Asp Glu Cys Tyr Phe Glu
465                 470                 475                 480
Asp Val Thr Ser Thr Asp Thr Tyr Phe Lys Asn Cys Thr Ile Glu Ser
                485                 490                 495
Thr Ile Phe Tyr Asn Thr Asp Leu Tyr Glu His Lys Phe Ile Asn Cys
            500                 505                 510
Arg Phe Ile Asn Ser Thr Phe Leu Glu Gln Lys Glu Gly Cys His Met
            515                 520                 525
Asp Leu Glu Gln Asp Asn Asp Phe Leu Ile Tyr Leu Val Ser Phe Leu
530                 535                 540
Gly Ser Leu Ser Val Leu Pro Gly Asn Ile Ile Ser Ala Leu Leu Met
545                 550                 555                 560
Asp Arg Ile Gly Arg Leu Lys Met Ile Gly Gly Ser Met Leu Ile Ser
                565                 570                 575
Ala Val Cys Cys Phe Phe Leu Phe Phe Gly Asn Ser Glu Ser Ala Met
                580                 585                 590
Ile Gly Trp Gln Cys Leu Phe Cys Gly Thr Ser Ile Ala Ala Trp Asn
            595                 600                 605
Ala Leu Asp Val Ile Thr Val Glu Leu Tyr Pro Thr Asn Gln Arg Ala
610                 615                 620
Thr Ala Phe Gly Ile Leu Asn Gly Leu Cys Lys Phe Gly Ala Ile Leu
625                 630                 635                 640
Gly Asn Thr Ile Phe Ala Ser Phe Val Gly Ile Thr Lys Val Val Pro
                645                 650                 655
Ile Leu Leu Ala Ala Ala Ser Leu Val Gly Gly Leu Ile Ala Leu
                660                 665                 670
Arg Leu Pro Glu Thr Arg Glu Gln Val Leu Met
                675                 680
```

<210> SEQ ID NO 8
<211> LENGTH: 683
<212> TYPE: PRT
<213> ORGANISM: Mus musculus
<220> FEATURE:
<221> NAME/KEY: misc_feature
<223> OTHER INFORMATION: HUMAN SV2B

<400> SEQUENCE: 8

```
Met Asp Asp Tyr Arg Tyr Arg Asp Asn Tyr Glu Gly Tyr Ala Pro Ser
1               5                   10                  15

Asp Gly Tyr Tyr Arg Ser Asn Glu Gln Asn Gln Glu Glu Asp Ala Gln
                20                  25                  30

Ser Asp Val Thr Glu Gly His Asp Glu Glu Asp Glu Ile Tyr Glu Gly
            35                  40                  45

Glu Tyr Gln Gly Ile Pro His Pro Asp Asp Val Lys Ser Lys Gln Thr
        50                  55                  60

Lys Met Ala Pro Ser Arg Ala Asp Gly Leu Gly Gly Gln Ala Asp Leu
65                  70                  75                  80

Met Ala Glu Arg Met Glu Asp Glu Glu Leu Ala His Gln Tyr Glu
                85                  90                  95

Thr Ile Ile Asp Glu Cys Gly His Gly Arg Phe Gln Trp Thr Leu Phe
            100                 105                 110

Phe Val Leu Gly Leu Ala Leu Met Ala Asp Gly Val Glu Ile Phe Val
        115                 120                 125

Val Ser Phe Ala Leu Pro Ser Ala Glu Lys Asp Met Cys Leu Ser Ser
    130                 135                 140

Ser Lys Lys Gly Met Leu Gly Leu Ile Val Tyr Leu Gly Met Met Ala
145                 150                 155                 160

Gly Ala Phe Ile Leu Gly Gly Leu Ala Asp Lys Leu Gly Arg Lys Lys
                165                 170                 175

Val Leu Ser Met Ser Leu Ala Ile Asn Ala Ser Phe Ala Ser Leu Ser
            180                 185                 190

Ser Phe Val Gln Gly Tyr Gly Ala Phe Leu Phe Cys Arg Leu Ile Ser
        195                 200                 205

Gly Ile Gly Ile Gly Gly Ser Leu Pro Ile Val Phe Ala Tyr Phe Ser
    210                 215                 220

Glu Phe Leu Ser Arg Glu Lys Arg Gly Glu His Leu Ser Trp Leu Gly
225                 230                 235                 240

Ile Phe Trp Met Thr Gly Gly Ile Tyr Ala Ser Ala Met Ala Trp Ser
                245                 250                 255

Ile Ile Pro His Tyr Gly Trp Gly Phe Ser Met Gly Thr Asn Tyr His
            260                 265                 270

Phe His Ser Trp Arg Val Phe Val Ile Val Cys Ala Leu Pro Ala Thr
        275                 280                 285

Val Ser Met Val Ala Leu Lys Phe Met Pro Glu Ser Pro Arg Phe Leu
    290                 295                 300

Leu Glu Met Gly Lys His Asp Glu Ala Trp Met Ile Leu Lys Gln Val
305                 310                 315                 320

His Asp Thr Asn Met Arg Ala Lys Gly Thr Pro Glu Lys Val Phe Thr
                325                 330                 335

Val Ser His Ile Lys Thr Pro Lys Gln Met Asp Glu Phe Ile Glu Ile
            340                 345                 350

Gln Ser Ser Thr Gly Thr Trp Tyr Gln Arg Trp Leu Val Arg Phe Met
        355                 360                 365
```

```
Thr Ile Phe Lys Gln Val Trp Asp Asn Ala Leu Tyr Cys Val Met Gly
        370                 375                 380

Pro Tyr Arg Met Asn Thr Leu Ile Leu Ala Val Val Trp Phe Thr Met
385                 390                 395                 400

Ala Leu Ser Tyr Tyr Gly Leu Thr Val Trp Phe Pro Asp Met Ile Arg
                405                 410                 415

Tyr Phe Gln Asp Glu Glu Tyr Lys Ser Lys Met Lys Val Phe Phe Gly
                420                 425                 430

Glu His Val His Gly Ala Thr Ile Asn Phe Thr Met Glu Asn Gln Ile
                435                 440                 445

His Gln His Gly Lys Leu Val Asn Asp Lys Phe Ile Lys Met Tyr Phe
                450                 455                 460

Lys His Val Leu Phe Glu Asp Thr Phe Phe Asp Lys Cys Tyr Phe Glu
465                 470                 475                 480

Asp Val Thr Ser Thr Asp Thr Tyr Phe Lys Asn Cys Thr Ile Glu Ser
                485                 490                 495

Thr Thr Phe Tyr Asn Thr Asp Leu Tyr Lys His Lys Phe Ile Asn Cys
                500                 505                 510

Arg Phe Ile Asn Ser Thr Phe Leu Glu Gln Lys Glu Gly Cys His Met
                515                 520                 525

Asp Phe Glu Glu Asp Asn Asp Phe Leu Ile Tyr Leu Val Ser Phe Leu
530                 535                 540

Gly Ser Leu Ser Val Leu Pro Gly Asn Ile Ile Ser Ala Leu Leu Met
545                 550                 555                 560

Asp Arg Ile Gly Arg Leu Lys Met Ile Gly Ser Met Leu Ile Ser
                565                 570                 575

Ala Val Cys Cys Phe Phe Leu Phe Phe Gly Asn Ser Glu Ser Ala Met
                580                 585                 590

Ile Gly Trp Gln Cys Leu Phe Cys Gly Thr Ser Ile Ala Ala Trp Asn
                595                 600                 605

Ala Leu Asp Val Ile Thr Val Glu Leu Tyr Pro Thr Asn Gln Arg Ala
                610                 615                 620

Thr Ala Phe Gly Ile Leu Asn Gly Leu Cys Lys Phe Gly Ala Ile Leu
625                 630                 635                 640

Gly Asn Thr Ile Phe Ala Ser Phe Val Gly Ile Thr Lys Val Val Pro
                645                 650                 655

Ile Leu Leu Ala Ala Ala Ser Leu Val Gly Gly Leu Ile Ala Leu
                660                 665                 670

Arg Leu Pro Glu Thr Arg Glu Gln Val Leu Met
                675                 680

<210> SEQ ID NO 9
<211> LENGTH: 683
<212> TYPE: PRT
<213> ORGANISM: Rattus norvegicus
<220> FEATURE:
<221> NAME/KEY: misc_feature
<223> OTHER INFORMATION: RAT SV2B

<400> SEQUENCE: 9

Met Asp Asp Tyr Arg Tyr Arg Asp Asn Tyr Glu Gly Tyr Ala Pro Asn
1               5                   10                  15

Asp Gly Tyr Tyr Arg Gly Asn Glu Gln Asn Pro Glu Glu Asp Ala Gln
                20                  25                  30

Ser Asp Val Thr Glu Gly His Asp Glu Glu Asp Glu Ile Tyr Glu Gly
```

```
            35                  40                  45
Glu Tyr Gln Gly Ile Pro His Pro Asp Asp Val Lys Ser Lys Gln Thr
 50                  55                  60
Lys Met Ala Pro Ser Arg Ala Asp Gly Leu Arg Gly Gln Ala Asp Leu
 65                  70                  75                  80
Met Ala Glu Arg Met Glu Asp Glu Glu Gln Leu Ala His Gln Tyr Glu
                 85                  90                  95
Thr Ile Ile Asp Glu Cys Gly His Gly Arg Phe Gln Trp Thr Leu Phe
                100                 105                 110
Phe Val Leu Val Leu Ala Leu Met Ala Asp Gly Val Glu Val Phe Val
            115                 120                 125
Val Ser Phe Ala Leu Pro Ser Ala Glu Lys Asp Met Cys Leu Ser Ser
    130                 135                 140
Ser Lys Lys Gly Met Leu Gly Leu Ile Val Tyr Leu Gly Met Met Ala
145                 150                 155                 160
Gly Ala Phe Ile Leu Gly Gly Leu Ala Asp Lys Leu Gly Arg Lys Lys
                165                 170                 175
Val Leu Ser Met Ser Leu Ala Ile Asn Ala Ser Phe Ala Ser Leu Ser
            180                 185                 190
Ser Phe Val Gln Gly Tyr Gly Ala Phe Leu Phe Cys Arg Leu Ile Ser
    195                 200                 205
Gly Ile Gly Ile Gly Gly Ser Leu Pro Ile Val Phe Ala Tyr Phe Ser
210                 215                 220
Glu Phe Leu Ser Arg Glu Lys Arg Gly Glu His Leu Ser Trp Leu Gly
225                 230                 235                 240
Ile Phe Trp Met Thr Gly Gly Ile Tyr Ala Ser Ala Met Ala Trp Ser
                245                 250                 255
Ile Ile Pro His Tyr Gly Trp Gly Phe Ser Met Gly Thr Asn Tyr His
                260                 265                 270
Phe His Ser Trp Arg Val Phe Val Ile Val Cys Ala Leu Pro Ala Thr
            275                 280                 285
Val Ser Met Val Ala Leu Lys Phe Met Pro Glu Ser Pro Arg Phe Leu
    290                 295                 300
Leu Glu Met Gly Lys His Asp Glu Ala Trp Met Ile Leu Lys Gln Val
305                 310                 315                 320
His Asp Thr Asn Met Arg Ala Lys Gly Thr Pro Glu Lys Val Phe Thr
                325                 330                 335
Val Ser His Ile Lys Thr Pro Lys Gln Met Asp Glu Phe Ile Glu Ile
                340                 345                 350
Gln Ser Ser Thr Gly Thr Trp Tyr Gln Arg Trp Leu Val Arg Phe Met
            355                 360                 365
Thr Ile Phe Lys Gln Val Trp Asp Asn Ala Leu Tyr Cys Val Met Gly
    370                 375                 380
Pro Tyr Arg Met Asn Thr Leu Ile Leu Ala Val Val Trp Phe Thr Met
385                 390                 395                 400
Ala Leu Ser Tyr Tyr Gly Leu Thr Val Trp Phe Pro Asp Met Ile Arg
                405                 410                 415
Tyr Phe Gln Asp Glu Glu Tyr Lys Ser Lys Met Lys Val Phe Phe Gly
                420                 425                 430
Glu His Val His Gly Ala Thr Ile Asn Phe Thr Met Glu Asn Gln Ile
            435                 440                 445
His Gln His Gly Lys Leu Val Asn Asp Lys Phe Ile Lys Met Tyr Phe
    450                 455                 460
```

-continued

```
Lys His Val Leu Phe Glu Asp Thr Phe Phe Asp Lys Cys Tyr Phe Glu
465                 470                 475                 480

Asp Val Thr Ser Thr Asp Thr Tyr Phe Lys Asn Cys Thr Ile Glu Ser
                485                 490                 495

Thr Thr Phe Tyr Asn Thr Asp Leu Tyr Lys His Lys Phe Ile Asp Cys
            500                 505                 510

Arg Phe Ile Asn Ser Thr Phe Leu Glu Gln Lys Glu Gly Cys His Met
            515                 520                 525

Asp Phe Glu Glu Asp Asn Asp Phe Leu Ile Tyr Leu Val Ser Phe Leu
        530                 535                 540

Gly Ser Leu Ser Val Leu Pro Gly Asn Ile Ile Ser Ala Leu Leu Met
545                 550                 555                 560

Asp Arg Ile Gly Arg Leu Lys Met Ile Gly Gly Ser Met Leu Ile Ser
                565                 570                 575

Ala Val Cys Cys Phe Phe Leu Phe Phe Gly Asn Ser Glu Ser Ala Met
                580                 585                 590

Ile Gly Trp Gln Cys Leu Phe Cys Gly Thr Ser Ile Ala Ala Trp Asn
            595                 600                 605

Ala Leu Asp Val Ile Thr Val Glu Leu Tyr Pro Thr Asn Gln Arg Ala
            610                 615                 620

Thr Ala Phe Gly Ile Leu Asn Gly Leu Cys Lys Leu Gly Ala Ile Leu
625                 630                 635                 640

Gly Asn Thr Ile Phe Ala Ser Phe Val Gly Ile Thr Lys Val Val Pro
                645                 650                 655

Ile Leu Leu Ala Ala Ser Leu Val Gly Gly Gly Leu Val Ala Leu
                660                 665                 670

Arg Leu Pro Glu Thr Arg Glu Gln Val Leu Met
            675                 680
```

BOTULINUM NEUROTOXIN E RECEPTORS AND USES THEREOF

GOVERNMENT INTEREST

This invention was made with United States government support awarded by the National Institutes of Health under the grant number NIAID R01 AI057744. The United States government has certain rights in this invention.

BACKGROUND OF THE INVENTION

Botulinum neurotoxins (BoNTs), produced by the anaerobic bacterium *Clostridium botulinum*, are the most potent toxins known[1]. These toxins cause botulism, a severe disease in humans and animals. Botulism usually results from ingestion of contaminated food. The toxins are first absorbed in the digestive system, possibly through a form of transcytosis across epithelial cells that line the gastrointestinal tract. Once in the bloodstream, the toxins target and enter motor nerve terminals and block the release of acetylcholine at neuromuscular junctions (NMJs), causing flaccid paralysis and may lead to death due to respiratory failure[1, 2]. Botulism is a rare disease in humans and thus the general population has not been immunized against these toxins; this is one of the reasons that BoNTs are among the most dangerous potential bioterrorism threats[3].

There are seven serotypes of BoNTs (BoNT/A to G)[1, 2]. Each toxin is composed of a light chain (~50 kDa) and a heavy chain (~100 kDa), connected through a disulfide bond[1]. The heavy chain mediates cell-entry, via receptor-mediated endocytosis, and translocation of the light chain across the endosomal membrane into the cytosol[1]. The light chain is a protease that cleaves target proteins in cells[1]. BoNT/A and E cleave the peripheral membrane protein SNAP-25 (synaptosomal-associated protein of 25 kDa); BoNT/B,D,F and G cleave the vesicle membrane protein synaptobrevin (Syb); BoNT/C cleaves both SNAP-25 and the plasma membrane protein syntaxin[4-9]. SNAP-25, syntaxin and Syb are collectively referred to as SNARE (soluble N-ethylmaleimide-sensitive factor attachment receptor) proteins. These three SNAREs assemble into a complex that mediates the fusion of synaptic vesicles with the plasma membrane[10-12]; cleavage of these proteins thus inhibits synaptic vesicle exocytosis and blocks the release of neurotransmitters. Because of their ability to inhibit synaptic transmission, BoNTs are used to treat a wide spectrum of medical conditions ranging from overactive muscle disorders to chronic pain[13-17].

The extremely high efficacy of these toxins is not only due to their enzymatic activity, but also involves their ability to recognize and enter presynaptic nerve terminals with high affinity and specificity. Thus, a major focus of research has been to identify the neuronal receptors for BoNTs. A "double-receptor" hypothesis has been proposed, in which BoNTs recognize nerve terminals by binding to two components: a group of membrane glycosphingolipids called gangliosides, and specific protein receptors[18].

Complex forms of gangliosides, called polysialiogangliosides (PSG), have been shown to bind BoNT/A, B and E with low affinity[19-22]. Cells lacking gangliosides are resistant to the binding and entry of BoNT/A, B and G; entry can be rescued by loading cell membranes with exogenous gangliosides[23-25]. Furthermore, mice lacking PSG showed decreased sensitivities to BoNT/A, B, C and G[25-29]. Interestingly, it was recently reported that BoNT/D does not interact with gangliosides and loss of PSG does not diminish the entry of BoNT/D into neurons[27]. Furthermore, mice lacking PSG exhibit the same sensitivity to BoNT/D as wild type (WT) mice, indicating that not all BoNTs utilize gangliosides as co-receptors[27]. It has not been reported whether gangliosides are essential for the entry of BoNT/E or BoNT/F into neurons.

Among the seven BoNTs, the protein receptors for BoNT/A, B and G have been identified (see e.g. U.S. patent application Ser. No. 10/695,577). Two homologous synaptic vesicle membrane proteins, synaptotagmins I and II (Syts I/II), were first found to bind BoNT/B[30, 31] and were subsequently shown to function as the protein receptors that mediate entry of BoNT/B into cells[25, 32]. The toxin binding site lies in a short intravesicular region that is conserved between Syt I and II[32]. In addition, BoNT/G was also found to utilize Syt I/II as its receptor by recognizing the same toxin binding site on Syt I/II as BoNT/B[25, 29, 33].

The co-crystal structure of BoNT/B bound to the toxin binding domain of Syt II was recently reported. This structure revealed that the toxin binds Syt II through a hydrophobic groove within the C-terminal region of BoNT/B[24, 34]. This hydrophobic groove is conserved in all subtypes of BoNT/B, as well as in BoNT/G[24, 29, 34].

The receptor for BoNT/A was recently identified as another synaptic vesicle membrane protein, SV2[35, 36]. All three isoforms of SV2 in mammals (SV2A, B and C) bind BoNT/A and mediate its entry into cells[35]. SV2 contains twelve transmembrane domains with one large luminal domain (the fourth luminal domain, L4) between the seventh and eighth transmembrane domains[37-40]. SV2 is a proteoglycan on synaptic vesicles and is heavily glycosylated, possibly through three putative N-glycosylation sites within the L4 luminal domain[37, 38, 40-42]. Interestingly, the BoNT/A binding site was mapped to a region within the SV2-L4 domain that contains two putative glycosylation sites[35]. It is not clear whether glycosylation of SV2 affects the binding of BoNT/A.

BoNT/E is one of four BoNTs (BoNT/A, B, E and rarely F) that are associated with human botulism[43]. It is also one of the leading causes of botulism outbreaks among wild fish and birds[44]. The protein receptor for BoNT/E, however, has not been identified.

Previous studies revealed that neuronal activity facilitated paralysis in diaphragm muscle preparations exposed to BoNT/E, and increased the cleavage of the substrate protein—SNAP-25—in cultured hippocampal neurons[45, 46], providing indirect evidence that synaptic vesicle recycling may enhance the entry of BoNT/E. However, it was reported that BoNT/E does not bind to the recombinant luminal domains of Syt I/II or SV2 purified from *E. coli*[32, 33, 35, 36].

Previously, BoNT/A and E was reported to bind Syt I in a ganglioside independent manner (Li and Singh, 1998, Isolation of synaptotagmin as a receptor for types A and E botulinum neurotoxin and analysis of their comparative binding using a new microtiter plate assay. J. Nat. Toxins. 7:215-26). This reported binding, however, turned out to be at best nonspecific, as subsequent work could not confirm any significant binding between BoNT/E and Syt I (see Dong et al., 2003, Synaptotagmins I and II mediate entry of botulinum neurotoxin B into cells, J. Cell. Bio. 162:1293-1303, at FIG. 1A). The lack of binding between BoNT/E and Syt I has also been further confirmed by others (see Rummel et al., 2004, Synaptotagmins I and II Act as Nerve Cell Receptors for Botulinum Neurotoxin G, J. Biol. Chem. 279:30865-30870, at FIG. 1B).

There is thus a need to identify the protein receptor for BoNT/E and to determine whether gangliosides serve as co-receptors for this toxin. Identification of the receptor for BoNT/E will be extremely useful for designing molecules that can reduce or completely inhibit its toxicity. Similarly, knowledge of the BoNT/E binding domain of the receptor will allow the use of polypeptides containing the domain and peptidomimetics thereof as competitors for BoNT binding, thereby reducing or completely inhibiting BoNT toxicity.

There is also a need to target the enzymatic domain of BoNTs, i.e. the light chain that can cleave SNARE proteins, into non-neuronal cells. Many types of cells use SNARE proteins to mediate vesicle release of hormones, cytokines, etc. It is well-known that vesicle-mediated release of transmitters and hormones constitutes a fundamental means of intercellular communication and malfunction of this process leads to many diseases. BoNTs have proven to be a powerful tool to treat diseases caused by over-active neurons. Currently, however, one cannot use BoNTs to treat non-neuronal cells for excessive secretion, mainly because BoNTs cannot enter these cells which do not express BoNT receptors. Even if non-neuronal cells did express BoNT receptors, it was not known if BoNT would be effective in these cells, as non-neuronal cells are known to lack synaptic vesicle recycling pathway, but no entry pathway other than synaptic vesicle recycling was known to result in functional entry of BoNT.

There is a further need for non-neuronal cells who express a BoNT receptor. Such cells would be more stable and more easily to culture, and can be used to replace using primary culture neurons for studying toxin actions and screening toxin inhibitors.

SUMMARY OF THE INVENTION

The present inventors have surprisingly found that two glycosylated isoforms of the synaptic vesicle protein, SV2, in conjunction with ganglio sides, mediate the entry of BoNT/E into neurons. Specifically, the inventors identified two isoforms of SV2, SV2A and SV2B, as the protein receptors for BoNT/E. BoNT/E failed to enter hippocampal neurons cultured from SV2A/B knockout mice; but entry was restored by expressing SV2A or SV2B, but not SV2C. Diaphragm motor nerve terminals from SV2B knockout mice displayed reduced sensitivity to BoNT/E and mice lacking SV2B survived longer than wild type mice when challenged with the same amount of BoNT/E. The fourth luminal domain of SV2A or SV2B (SV2-L4), expressed in chimeric receptors by replacing the extracellular domain of the low-density lipoprotein receptor, co-immunoprecipitates with BoNT/E and restores the binding and entry of BoNT/E into neurons lacking SV2A/B.

In addition, it was found that glycosylation at the third N-glycosylation site within the SV2-L4 domain is essential for binding of BoNT/E, and also plays a role in the entry of BoNT/A into neurons. The inventors mutated the third N-glycosylation site in SV2A, which is within the luminal domain of SV2A (a N573Q mutation), and found that the mutant was unable to mediate the entry of BoNT/E into neurons. This mutant also reduced the entry of BoNT/A, another botulinum neurotoxin that can utilize all three isoforms of SV2 as receptors. On the other hand, the L4 domain alone, engineered to replace the extracellular domain of low density lipoprotein receptor (LDLR), is sufficient to mediate the entry of BoNT/A and E.

Finally, the inventors found that gangliosides are essential for binding and entry of BoNT/E into neurons, thus extending the "double-receptor" model to BoNT/E. BoNT/E failed to bind and enter neurons cultured from ganglioside deficient mice, but this defect can be rescued by loading exogenous gangliosides into neuronal membranes.

Thus, the present invention provides, in one embodiment, an isolated polypeptide comprising an amino acid sequence selected from (i) amino acids 506-582 of SV2A, wherein position 573 is N and is glycosylated; (ii) amino acids 449-525 of SV2B, wherein position 516 is N and is glycosylated; and (iii) an amino acid sequence that is at least 70%, at least 80%, at least 90%, at least 95%, at least 97%, at least 98%, or at least 99% identical to either of the amino acid sequences in (i) to (ii) and is capable of binding to botulinum neurotoxin E (BoNT/E), provided that full-length SV2A and SV2B proteins are excluded. Preferably, the isolated polypeptide is soluble. In one embodiment, the isolated polypeptide of the present invention further comprises a ganglioside binding site.

The present invention also provides an antibody that binds specifically to the polypeptide of the present invention described above.

The present invention also provides an isolated nucleic acid comprising a polynucleotide or its complement wherein the polynucleotide encodes the polypeptide of the present invention; a vector comprising the nucleic acid operably linked to a normative promoter, and a host cell comprising the vector.

In another embodiment, the present invention also provides a method for reducing BoNT/E toxicity in an animal comprising administering to the animal an agent that reduces binding between BoNT/E and an SV2A or SV2B in vivo. Preferably, the animal is a mammal, more preferably a human. In one embodiment, the agent for the above method comprises a polypeptide of present invention as described above, or a polypeptide that comprises a full length SV2A or SV2B protein. In one embodiment, the agent for the above method is an antagonist against ganglio side, such as an anti-ganglio side antibody, or an antibody against a peptide of the present invention described above, or an antibody against a full-length SV2A or SV2B. In another embodiment, the agent reduces the expression of an SV2A or an SV2B protein in the animal. In a further embodiment, the antagonist is siRNA against SV2A or SV2B. In yet another embodiment, the agent reduces the binding between gangliosides and an SV2A or SV2B protein, or reduces the amount of ganglio sides available for binding to the SV2A or SV2B protein in vivo.

In another embodiment, the present invention also provides a method of inhibiting BoNT toxin activity comprising reducing the amount of activity of a cellular protein glycosylation enzyme.

In another embodiment, the present invention also provides a method for identifying an agent that blocks or inhibits binding between BoNT/E and an SV2A or SV2B protein, the method comprising: measuring binding between BoNT/E and a polypeptide in the presence of a test agent wherein the polypeptide is selected from a polypeptide of claim 1, a polypeptide that comprises a full length SV2A or Sv2B protein, a polypeptide consisting of an SV2A L4 domain, and a polypeptide that comprises an SV2B L4 wherein the domain is flanked at one or both ends by a non-native flanking amino acid sequence; and comparing the binding to that of a control measured under the same conditions but in the absence of the test agent, wherein a lower-than-control binding indicates that the agent can block binding between BoNT/E and the SV2 protein. In one embodiment, all steps above are performed in vitro. Alternatively, the polypeptide is provided on a cell surface and the cell is exposed to the test agent, for example, the binding between BoNT/E and the polypeptide is measured indirectly by monitoring the entry of BoNT/E into the cell.

In another embodiment, the present invention also provides a method for monitoring synaptic vesicle endo- or exocytosis, comprising administering to synaptic cells a fluorescently labeled BoNT/A, B, E or G toxin, or a fragment thereof that contains a receptor binding domain as a marker, and allowing the marker to bind to a specific receptor for the BoNT.

In another embodiment, the present invention also provides a method for monitoring synaptic vesicle endo- or exocytosis, comprising administering to synaptic cells a BoNT/A, B, E or G toxin, or a fragment thereof that contains a receptor binding domain as a marker, allowing the marker to bind to a specific receptor for the BoNT, and detecting the marker with a suitably labeled antibody against the BoNT. For example, the antibody may be fluorescently labeled.

In another embodiment, the present invention also provides a method for specifically delivering a chemical entity to a cell which has a specific receptor to a BoNT/A, B, E or G toxin, the method comprising administering to the cell a construct comprising a chimera of a BoNT toxin and the chemical entity, whereby the chemical entity is delivered to the cell. The cell may be a neuron cell, or a non-neuronal cell, or a cell modified, e.g. via genetic engineering to express a specific BoNT toxin receptor.

In another embodiment, the present invention also provides a chimeric toxin for targeting a proteolytic domain of a toxin to a cell, the chimeric toxin comprising a catalytic or proteolytic domain of the BoNT toxin, and a ligand or a fragment thereof for a non-BoNT receptor on the cell.

In another embodiment, the present invention also provides a method for targeting a proteolytic domain of a BoNT toxin to a cell, comprising administering the chimeric toxin of claim 33 to the cell, whereby SNARE-mediated exocytosis or protein delivery to target membranes is blocked.

In another embodiment, the present invention also provides an isolated non-neuronal cell comprising a BoNT toxin receptor.

In another embodiment, the present invention also provides a method for screening for an inhibitor of a BoNT toxin, the method comprising applying to the isolated non-neuronal cell expressing a BoNT toxin receptor a candidate compound, in the presence of the BoNT toxin, measure the effect of the BoNT toxin on the cell, and compare the effect of the BoNT on the cell in the presence of the candidate compound to a control where the cell is not treated with the candidate compound, wherein a decrease in the effect of the BoNT cell on the cell indicates that the compound inhibits the effect of the BoNT cell.

The invention is described in more details below with the help of the drawings and examples, which are not to be construed to be limiting the scope of the present invention.

BRIEF DESCRIPTION OF THE DRAWINGS

FIG. 6 shows that glycosylation of the third glycosylation site within the SV2A-L4 domain is essential for entry of BoNT/E, and affects the sensitivity of neurons to BoNT/A. a) Partial amino acid sequence of the SV2A-L4 domain (SEQ ID NO:1), with putative N-glycosylation sites and point mutation sites, described in the following panels, indicated. The amino acid sequences of the corresponding regions of SV2B (SEQ ID NO: 2) and SV2C (SEQ ID NO: 3) are also shown. b) Three putative glycosylation sites within the SV2A-L4 domain were abolished by site-directed mutagenesis (N to Q), respectively. These mutants were expressed in SV2 A/B KO neurons via lentiviral infection. Neurons were exposed to BoNT/E (200 μM) and were assayed as described in FIG. 2b. Point mutations of each putative glycosylation site resulted in reduced apparent molecular weights, indicating that all three sites are glycosylated in neurons. Substitution of the third glycosylation site (N573Q) abolished the entry of BoNT/E into neurons. c) Experiments were carried out as described in panel b, except that neurons were exposed to a higher concentration of BoNT/E (1 nM). SV2A(+/+)SV2B (−/−) neurons were also tested in parallel as a control. d) SV2 A/B KO neurons were infected with WT, or the N498/548Q double mutant form of SV2A, using lentiviruses. The SV2A (N498/548Q) double mutant mediated entry of BoNT/E. e) A new N-linked glycosylation site was created by exchanging R570 for T in the SV2A(N573Q) mutant. When expressed in SV2A/B KO neurons via lentiviral infection, this mutant displayed a similar molecular weight to WT SV2, indicating that the new N-linked glycosylation site is glycosylated in neurons; however, this mutant failed to mediate the entry of BoNT/E. f) Experiments were carried out as described in panel b, except that cells were exposed to BoNT/A (7 nM, 5 min exposure, incubated for 12 hrs). The N573Q mutation reduced the entry of BoNT/A into neurons, reflected by the partial cleavage of SNAP-25. g) Experiments were carried out as described in panel f, but using a range of BoNT/A concentrations. When treated with 10 nM BoNT/A, a similar degree of cleavage of SNAP-25 was observed for neurons infected with WT or the N573Q mutant form of SV2. When exposed to 1 nM BoNT/A, more extensive cleavage was observed in neurons expressing WT SV2, as compared to neurons expressing the N573Q mutant.

FIG. 8A depicts the amino acid sequences of SV2A from three mammal Species (human, mouse and rat) (SEQ ID NOs: 4, 5, 6, respectively). FIG. 8B depicts the amino acid sequences of SV2B from three mammal Species (human, mouse and rat) (SEQ ID NOs: 7, 8, 9 respectively). The minimum SV2A segment needed for BoNT/E binding, as well as the L4 domain of SV2B, are highlighted.

DETAILED DESCRIPTION OF THE INVENTION

Figure 1:
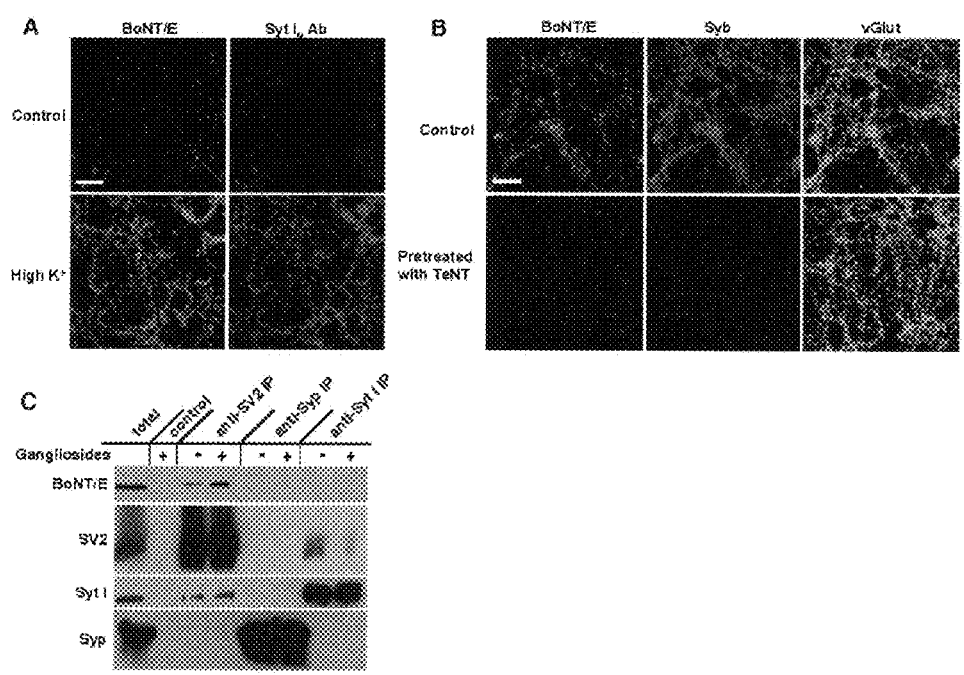
FIG. 1 shows that BoNT/E enters neurons via recycling synaptic vesicles and co-immunoprecipitates with the synaptic vesicle membrane protein SV2. a) Cultured rat hippocampal neurons were exposed to BoNT/E (30 nM) and an antibody against the luminal domain of Syt I (Syt $I_N$ Ab, 1:200) for 5 min in either resting conditions (control buffer: PBS) or stimulated conditions (high K$^+$ buffer: PBS with 56 mM KCl and 1 mM Ca$^{2+}$). Cells were washed and fixed for immunocytochemistry. Binding of BoNT/E was detected using a rabbit anti-BoNT/E antibody. Depolarization-induced synaptic vesicle recycling increased the binding of BoNT/E and the Syt $I_N$ Ab to neurons. High K$^+$ buffer was used in all following experiments unless otherwise indicated in the Figure Legends. Scale bars in all figures represent 20 µm. b) Rat hippocampal neurons were first incubated with tetanus neurotoxin (TeNT, 15 nM) for 24 hrs. Binding of BoNT/E to these neurons was tested under stimulated conditions (30 nM, 5 min in high K$^+$ buffer). Control cells were not treated with TeNT. Pre-treatment with TeNT resulted in the cleavage of Syb and diminished the binding of BoNT/E. c) Monoclonal antibodies were used to immunoprecipitate synaptic vesicle membrane proteins SV2 (pan-SV2), synaptophysin (Syp) and Syt I (Cl 41.1) from rat brain detergent extracts in the presence of BoNT/E (250 nM), with (+) or without (−) the addition of exogenous gangliosides (0.6 mg/ml). Immunoprecipitated vesicle proteins and BoNT/E were detected by SDS-PAGE and immunoblot analysis. BoNT/E co-immunoprecipitated with SV2. Addition of exogenous ganglio sides enhanced BoNT/E·SV2 interactions.

The present inventors found that glycosylated SV2A and SV2B are functional protein receptors for BoNT/E in neurons, and the L4 domain in SV2A and SV2B mediates the entry of BoNT/E into neurons. Specifically, SV2A and SV2B were found to mediate the binding and entry of BoNT/E into neurons, and mice lacking SV2B are less sensitive to BoNT/E.

The inventors also found that the entry of BoNT/E is mediated by the L4 domain in SV2A and SV2B, and that the L4 domain is sufficient to act as the toxin binding site on neuronal surfaces, because BoNT/E co-immunoprecipitated with the major luminal domain (L4 domain) of SV2A and SV2B expressed in HEK cells and because SV2A-L4 or SV2B-L4 luminal domains alone, expressed on the cell surface through fusion with the transmembrane and cytosolic domain of the LDLR, can mediate activity-independent entry of BoNT/E into SV2A/B KO neurons. These findings also revealed that entry pathways other than synaptic vesicle recycling can result in the functional entry of BoNT/A and E, and opened the possibility for targeting toxins to specific neurons or even non-neuronal cells through the recycling endosomal pathway, to block SNARE-mediated exocytosis or protein delivery to target membranes. For example, a chimeric receptor comprising the L4 domain can be engineered and expressed in a target cells, which can then mediate the entry of BoNT/A or E into these cells. These target cells can be either neuron or non-neuron cells.

It is further discovered that glycosylation of the third glycosylation site of SV2A (N573) is essential for entry of BoNT/E. SV2 contains three putative N-linked glycosylation sites, all of them located in the L4 domain[37, 38, 40], and all three sites are found to be glycosylated in neurons. A point mutation that abolishes the third glycosylation site (N573Q) in the SV2A-L4 domain rendered SV2A unable to mediate the entry of BoNT/E into neurons.

The role of gangliosides in the binding and entry of BoNT/E was also addressed using cultured hippocampal neurons from ganglioside deficient mice as a model system, and it was found that BoNT/E failed to bind and enter neurons lacking ganglio sides and that this defect can be rescued by loading neurons with exogenous gangliosides. These data support a "double-receptor" model for BoNT/E in which functional receptors are composed of both protein receptor SV2A/B and ganglio sides in neurons.

A detailed description of SV2 proteins, including its structure, amino acid sequence as well as the nucleic acid molecules encoding them, is provided in U.S. Pat. App. No. 60/726,879, which is incorporated herein by reference in its entirety. The amino acid sequences of human, rat and mouse SV2A and SV2B proteins are provided in FIG. 8. The SV2A protein comprises 743 amino acid residues, the LV4 domain of starts at position 468 and ends at 595. The SV2B protein comprises 683 amino acid residues, and the LV4 domain is generally thought to be located from position 410 to 539. It has been discovered that a polypeptide comprising a fragment that is equivalent to amino acid residues 506-582 of SV2A is sufficient to bind to and mediate cellular entry of BoNT/E.

Thus, the present invention provides an isolated polypeptide that comprises amino acid sequence residues of position 506 to position 582 of SEQ ID NO:4 SV2A-L4): HRGGQY-FNDKFIGLRLKSVSFEDSLFEECYFED-VTSSNTFFRNCTFINTVFYNTDLFEYKF VNSRLVNST-FLHNKEG, wherein position N573 (bold face) is glycosylated. Preferably, the isolated polypeptide comprises amino acid residues of position 468 to position 595 of the SVA protein 449 to position 525. These isolated polypeptides are collectively referred to herein as BoNT/E biding fragment, wherein the third glycosylation site corresponding to N573 of SV2A is glycosylated.

In one aspect, the present invention relates to an isolated polypeptide containing an amino acid sequence that is at least 60%, 65%, 70%, 75%, 80%, 85%, 90%, or 95% identical to that of a BoNT/E-binding fragment over the entire length of the binding fragment or an amino acid sequence of a BoNT/E-binding fragment with one or more conservative substitutions. Specifically excluded from the polypeptide of the present invention is naturally occurring, glycosylated and full-length SV2A or B proteins.

In one embodiment, the polypeptide of the present invention is about the size of an SV2A or SV2B L4 domain or shorter.

In another embodiment, the polypeptide of the present invention is soluble in an aqueous solvent (e.g., water with or without other additives). By soluble in an aqueous solvent, we mean that the polypeptide exhibits a solubility of at least 10 pg/ml, preferably at least 50 pg/ml or 100 pg/ml, more preferably at least 500 pg/ml, and most preferably at least 1,000 pg/ml in an aqueous solvent. Whether a polypeptide is soluble in an aqueous solution can be readily determined by a skilled artisan based on its amino acid sequence or through routine experimentation. Examples of soluble polypeptides of the present invention include those that contain all or part of the L4 domain of an SV2A of SV2B protein but lack at least part of and preferably the entire adjacent transmembrane domain(s). Soluble polypeptides are typically more suitable than insoluble polypeptides for intravenous administration.

The isolated polypeptide of the invention can include one or more amino acids at either or both N-terminal and C-terminal ends of a BoNT/E-binding sequence of an SV2A or SV2B protein, where the additional amino acid(s) do not materially affect the BoNT/E binding function. Any additional amino acids can, but need not, have advantageous use in purifying, detecting, or stabilizing the polypeptide.

In order to improve the stability and/or binding properties of a polypeptide, the molecule can be modified by the incorporation of non-natural amino acids and/or non-natural chemical linkages between the amino acids. Such molecules are called peptidomimics (H. U. Saragovi et al., *Bio/Technology* 10:773-778, 1992; S. Chen et al., *Proc. Nat'l. Acad. Sci. USA* 89:5872-5876, 1992). The production of such compounds is restricted to chemical synthesis. It is understood that a polypeptide of the present invention can be modified into peptidomimics without abolishing its function. This can be readily achieved by a skilled artisan.

In another aspect, the present invention relates to an isolated nucleic acid or its complement encoding a polypeptide of the invention as set forth above. A nucleic acid containing a polynucleotide that can hybridize to the coding polynucleotide or its complement, under either stringent or moderately stringent hybridization conditions, is useful for detecting the coding polypeptide and thus is within the scope of the present invention. Stringent hybridization conditions are defined as hybridizing at 68° C. in 5×SSC/5×Denhardt's solution/1.0% SDS, and washing in 0.2×SSC/0.1% SDS+/−100 ug/ml denatured salmon sperm DNA at room temperature, and moderately stringent hybridization conditions are defined as washing in the same buffer at 42° C. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10. A nucleic acid containing a polynucleotide that is at least SO %, 85%, 90%, or 95% identical to the coding polynucleotide or its complement over the entire length of the coding polynucleotide can also be used as a probe for detecting the coding polynucleotide and is thus within the scope of the present invention. Specifically excluded from the present invention is a nucleic acid that contains a nucleotide sequence encoding a full length SV2A or SV2B protein. In one embodiment, a nucleic acid that consists of a polynucleotide that encodes an SV2A or SV2B L4 domain.

In a related aspect, any nucleic acid of the present invention described above can be provided in a vector in a manner known to those skilled in the art. The vector can be a cloning vector or an expression vector. In an expression vector, the polypeptide-encoding polynucleotide is under the transcriptional control of one or more non-native expression control sequences which can include a promoter not natively found adjacent to the polynucleotide such that the encoded polypeptide can be produced when the vector is provided in a compatible host cell or in a cell-free transcription and translation system. Such cell-based and cell-free systems are well known to a skilled artisan. Cells comprising a vector containing a nucleic acid of the invention are themselves within the scope of the present invention. Also within the scope of the present invention is a host cell having the nucleic acid of the present invention integrated into its genome at a non-native site.

Methods for Reducing BoNT/E Toxicity

In another aspect, the present invention relates to a method for reducing BoNT/E toxicity in target cells such as neurons. As a result, botulism disease can be prevented or treated. In one embodiment, the method is used to reduce BoNT/E toxicity in a human or non-human animal by administering to the human or non-human animal an agent that can reduce BoNT/E toxicity.

The term "reducing BoNT/E cellular toxicity" encompasses any level of reduction in BoNT/E toxicity. The BoNT/E toxicity can be reduced by reducing the level of an SV2 protein in target cells, by inhibiting BoNT/E-related cellular functions of an SV2A or SV2B protein in target cells, or by reducing the binding between BoNT/E and an SV2A or SV2B protein located on the cellular surface of target cells. The binding between BoNT/E and an SV2A or SV2B protein can be reduced by either blocking the binding directly or by reducing the amount of SV2A or SV2B proteins available for binding.

There are many methods by which cellular protein levels such as the level of an SV2A or SV2B protein can be reduced. The present invention is not limited to a particular method in this regard. As an example, the cellular level of an SV2A protein can be reduced by using the antisense technology. For instance, a 20-25 mer antisense oligonucleotide directed against the 5' end of an SV2 mRNA can be generated. Phosphorothioate derivatives can be employed on the last three base pairs on the 3' and 5' ends of the antisense oligonucleotide to enhance its half-life and stability. A carrier such as a cationic liposome can be employed to deliver the antisense oligonucleotide. Another way to use an antisense oligonucleotide is to engineer it into a vector so that the vector can produce an antisense RNA that blocks the translation of an SV2A mRNA. Similarly, RNA interference (RNAi) or small interfering RNA (siRNA) techniques are also suited for inhibiting the expression of an SV2A protein.

Blocking the Binding Between BoNT/E and SV2A or SV2B

The identification of SV2A and SV2B as BoNT/E receptors as well as the BoNT/E-binding sequences on SV2A or SV2B enable those skilled in the art to block the binding between BoNT/E and its receptor. For example, monoclonal and polyclonal antibodies specific for the BoNT/E-binding sequences on SV2A or SV2B may be used to inhibit or prevent binding between BoNT/E and its receptors. It is well within the capability of a skilled artisan to generate such monoclonal and polyclonal antibodies. The antibodies so generated are within the scope of the present invention.

Another strategy involves the use of a BoNT/E-binding polypeptide, preferably a soluble BoNT/E-binding polypeptide, to compete with the receptor for BoNT/E binding. For example, the BoNT/E-binding polypeptide of the present invention described above can be employed for this purpose. Other polypeptides that can be employed include those that comprise a full length SV2A or SV2B protein, those that consist of an SV2A or SV2B luminal domain, and those that comprise an SV2A or SV2B L4 domain wherein the amino acid corresponding to the N573 residue is glycosylated.

To block the binding between BoNT/E and its receptor in an animal (human or non-human), a BoNT/E-binding polypeptide from both the same and a different species can be used. The polypeptide can be introduced into the animal by administering the polypeptide directly or by administering a vector that can express the polypeptide in the animal.

Those skilled in the art understand that mutations such as substitutions, insertions and deletions can be introduced into a BoNT/E-binding sequence of an SV2A or SV2B protein without abolishing their BoNT/E binding activity. Some mutations may even enhance the binding activity. A polypeptide containing such modifications can be used in the method of the present invention. Such polypeptides can be identified by using the screening methods described below.

In addition, as ganglio sides is needed to promote formation of stable BoNT/E-SV2A or SV2B complexes, the binding between BoNT/E and an SV2A or SV2B protein may be reduced through reducing the binding between the ganglio sides and the SV2A or SV2B protein or through reducing the amount of ganglio sides available for binding to the SV2A or SV2B protein. For example, antibodies raised against gangliosides may be used to reducing binding between BoNT/E and SV2A or SV2B.

In a related aspect, when a BoNT/E-binding polypeptide is used for reducing BoNT/E toxicity by forming a complex with BoNT/E, gangliosides may be included to facilitate the formation of the complex.

Identifying Agents that can Block Binding Between BoNT/E and SV2A or SV2B

Agents that can block binding between BoNT/E and SV2A or SV2B can be screened by employing BoNT/E and a polypeptide that contains a BoNT/E-binding sequence of an SV2A or SV2B protein under the conditions suitable for BoNT/E to bind the polypeptide. Gangliosides are optionally included in the reaction mixture. The binding between BoNT/E and the polypeptide can be measured in the presence of a test agent and compared to that of a control that is not exposed to the test agent. A lower-than-control binding in the test group indicates that the agent can block binding between BoNT/E and the SV2A or SV2B protein.

There are many systems with which a skilled artisan is familiar for assaying the binding between BoNT/E and a BoNT/E-binding polypeptide. Any of these systems can be used in the screening method. Detailed experimental conditions can be readily determined by a skilled artisan. For example, the binding between BoNT/E and the polypeptide described above can be measured in vitro (cell free system). A cell culture system in which an SV2A or SV2B protein is expressed and translocated onto the cellular membrane can also be used. For the cell culture system, in addition to the binding between BoNT/E and the SV2A or SV2B protein, the cellular entry of BoNT/E and a number of other parameters can also be used as an indicator of binding between BoNT/E and SV2A or SV2B.

Any method known to one of ordinary skill in the art for measuring protein—protein interaction can be used to measure the binding between BoNT/E and a BoNT/E-binding polypeptide. Co-immunoprecipitation and affinity column isolation are two commonly used methods.

Surface plasmon resonance (SPR) is another commonly used method. SPR uses changes in refractive index to quantify binding and dissociation of macromolecules to ligands covalently linked onto a thin gold chip within a micro flow cell. This technique has been used to study protein-protein interactions in many systems, including the interactions of PA63 with EF and LF (Elliott, J. L. et al., Biochemistry 39:6706-6713, 2000). It provides high sensitivity and accuracy and the ability to observe binding and release in real time. Besides the equilibrium dissociation constant (Kd), on- and off-rate constants (ka and kd) may also be obtained. Typically, a protein to be studied is covalently tethered to a carboxymethyl dextran matrix bonded to the gold chip. Binding of a proteinaceous ligand to the immobilized protein results in a change in refractive index of the dextradprotein layer, and this is quantified by SPR. A BIAcore 2000 instrument (Pharmacia Biotech) can be used for these measurements.

For the cell culture system, the binding of BoNT/E to a BoNT/E-binding polypeptide can be assayed by staining the cells, the examples of which are described in the example section below.

Identifying Agents that can Bind to a BoNT/E-Binding Sequence of SV2A or SV2B

Agents that can bind to a BoNT/E-binding sequence of an SV2A or SV2B protein can be used to block the binding between BoNT/E and the SV2A or SV2B protein. Such agents can be identified by providing a polypeptide that contains a BoNT/E-binding sequence of an SV2A or SV2B protein to a test agent, and determining whether the agent binds to the BoNT/E-binding sequence. Any agent identified by the method can be further tested for the ability to block BoNT/E entry into cells or to neutralize BoNT/E toxicity. A skilled artisan is familiar with the suitable systems that can be used for the further testing. Examples of such systems are provided in the example section below.

The skilled artisan is familiar with many systems in the art for assaying the binding between a polypeptide and an agent. Any of these systems can be used in the method of the present invention. Detailed experimental conditions can be readily determined by a skilled artisan. For example, a polypeptide that contains a BoNT/E-binding sequence of an SV2A or SV2B protein can be provided on a suitable substrate and exposed to a test agent. The binding of the agent to the polypeptide can be detected either by the loss of ability of the polypeptide to bind to an antibody or by the labeling of the polypeptide if the agent is radioactively, fluorescently, or otherwise labeled. In another example, a polypeptide that contains a BoNT/E-binding sequence of an SV2A OR SV2B protein can be expressed in a host cell, and the cell is then exposed to a test agent. Next, the polypeptide can be isolated, e.g., by immunoprecipitation or electrophoresis, and the binding between the polypeptide and the agent can be determined. As mentioned above, one way to determine the binding between the polypeptide and the agent is to label the agent so that the polypeptide that binds to the agent becomes labeled upon binding. If the test agent is a polypeptide, examples of specific techniques for assaying protein-protein binding as described above can also be used. It should be noted that when a BoNT/E-binding sequence of an SV2A or SV2B protein used in the screening assay have flanking sequences, it may be necessary to confirm that an agent binds to the BoNT/E-binding sequence rather than the flanking sequences, which can be readily accomplished by a skilled artisan.

Agents that can be Screened The agents screened in the above screening methods can be, for example, a high molecular weight molecule such as a polypeptide (including, e.g., a polypeptide containing a modified BoNT/E-binding sequence of an SV2A or SV2B protein, or a monoclonal or polyclonal antibody against a BoNT/E-binding sequence of an SV2A OR SV2B protein), a polysaccharide, a lipid, a nucleic acid, a low molecular weight organic or inorganic molecule, or the like.

Agents for screening are commercially available in the form of various chemical libraries including peptide libraries. Once an agent with desired activity is identified, a library of derivatives of that agent can be screened for better molecules. Phage display is also a suitable approach for finding novel inhibitors of the interaction between BoNT/E and SV2A or SV2B.

Methods of Detecting BoNT/E or *Clostridium botulinum*

In another aspect, the present invention relates to a method of detecting BoNT/E or the bacterium that produces it. The method involves exposing a sample suspected of containing BoNT/E to an agent that contains a polypeptide having a BoNT/E-binding sequence of an SV2A or SV2B protein, and detecting binding of the polypeptide to BoNT/E.

Use of BoNT Toxins as Markers for Labeling Synaptic Vesicles

Currently, a lipid-binding fluorescence dye (FM dye) is used for the purpose of monitoring synaptic vesicle recycling or exo/endocytosis. FM-dye binds to lipid and becomes fluorescent. Excessive dyes in solution are washed out, leaving FM-dyes only in "synaptic vesicles" that have been endocytosed. In this way, endocytosis of synaptic vesicles or exocytosis can be monitored. This method, though routinely used, has various drawbacks. For example, the dyes are not specific and are taken-up by all kinds of endocytosis events.

Because BoNT A, B, E, and G use specific synaptic vesicle proteins as receptors, they are able to specifically target synaptic vesicles. Accordingly, these toxins can be used to monitor synaptic vesicle recycling or exo/endocytosis. Thus, the present invention provides a method of using fluorescently labeled toxins or toxin fragments that contains the receptor binding domain as markers for synaptic vesicle endo/exocytosis monitoring. This method allows for very specific labeling of active synapses.

In an alternative embodiment, cells are treated with a suitable BoNT toxin or a fragment thereof, and the location of the toxins is detected with toxin-specific antibodies. The method of the present invention can be used to measure the number of active synapses, how much toxins can it endocytosis, and how fast it can endocytosis synaptic vesicles. The methods may be used in vitro for research purpose, as well as in vivo.

Furthermore, the toxins/toxin fragment can be used to target synaptic vesicles, such as to deliver specific drugs to synaptic vesicles/presynaptic buttons, or labeling synaptic vesicles as a way to label synapses and measuring the strength of synapses.

Chimeric Toxin Receptors; Cells Expressing Same; Chimeric Toxins for Targeting Non-Neuronal Cells.

In addition to the identification of receptors for BoNTs and their recognition, the present inventors surprisingly found that endocytosis pathways, other than synaptic vesicle recycling, can mediate the functional entry of BoNT/A and B. Accordingly, the present invention provides a method for targeting BoNT toxins into specific neurons or even non-neuronal cells, to block SNARE-mediated exocytosis or protein delivery to target membranes. Toxin entry into specific cells can be achieved by expressing chimeric receptors containing toxin-binding sites. Alternatively, the receptor binding domain of toxin molecules can be modified or replaced to create chimeric toxins that target distinct cell surface receptors.

Figure 4:
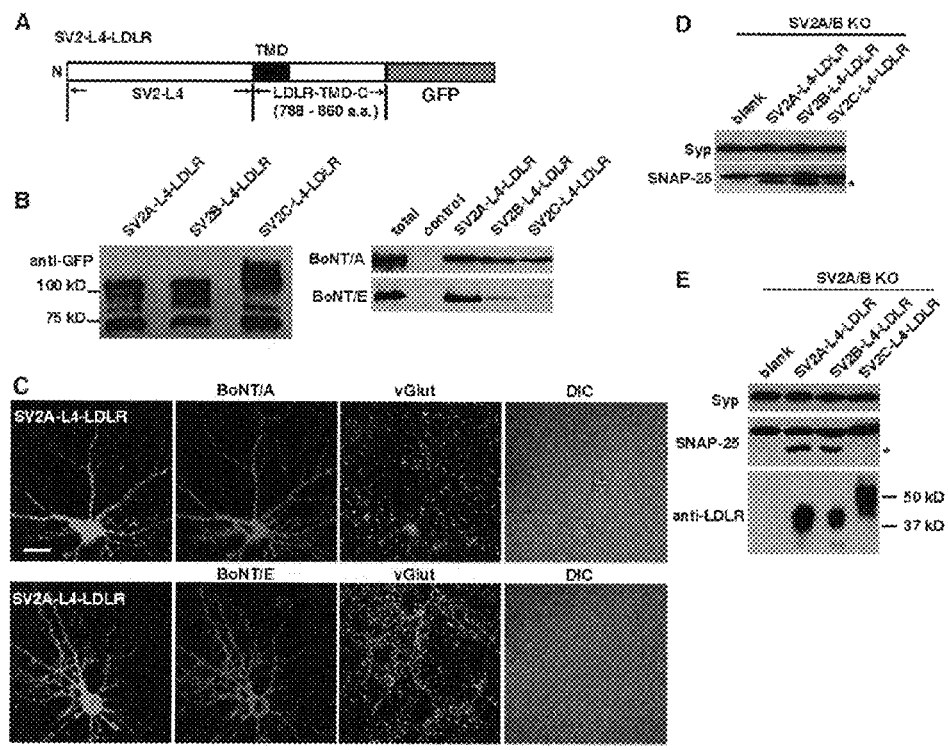
FIG. 4 demonstrates that the luminal domains of SV2 A and B mediate the binding and entry of BoNT/E into neurons. a) Schematic drawings of SV2 and the chimeric receptors. The chimeric receptors are composed of the L4 domain of SV2A/B/C, and the transmembrane domain (TMD) and the cytosolic domain of the LDL-receptor. The constructs used in panel b and c also contain a GFP tag that was fused, in frame, to the C-terminus of the chimeric receptor. b) Co-immunoprecipitation of BoNT/A (100 nM) or BoNT/E (250 nM) with SV2-L4-LDLR chimeric receptors, expressed in HEK293 cells, was carried out using a monoclonal antibody against GFP, in the presence of exogenous gangliosides (0.6 mg/ml). Left panel: immunoprecipitated chimeric receptors were subjected to SDS-PAGE and immunoblot analysis using a polyclonal GFP antibody. Right panel: BoNT/A co-immunoprecipitated with all three chimeric receptors; BoNT/E co-immunoprecipitated with SV2A-L4-LDLR, and to a much lesser degree with SV2B-L4-LDLR. c) SV2 A/B KO neurons were transfected with SV2A-L4-LDLR and exposed to BoNT/A (20 nM) or BoNT/E (30 nM) in normal culture media for 10 min. Cells were fixed for immunocytochemistry. vGlut was labeled as a marker for synapses. Expression of SV2A-L4-LDLR restored the binding of BoNT/A (upper panel) or BoNT/E (lower panel). d) SV2A/B KO neurons were infected with lentiviruses that express chimeric receptors containing the L4 domains of SV2A, B or C, respectively. Neurons were exposed to BoNT/A (10 nM) in culture media for 10 min, and were harvested 12 hrs later. Cell lysates were subjected to SDS-PAGE and immunoblot analysis. Cleavage of SNAP-25 was observed for neurons that were infected with SV2A, B or C chimeric receptors. e) Experiments were carried out as described in panel d, except that neurons were exposed to BoNT/E (2 nM). The cleavage of SNAP-25 was observed for neurons infected with lentiviruses that express SV2A-L4 or SV2B-L4 chimeric receptors, but not with viruses that express the SV2C-L4 chimeric receptor. Expression of chimeric receptors was determined by SDS-PAGE and immunoblot analysis using an antibody that recognizes the C-terminal region of the LDLR (lower panel).

In order to achieve targeted entry of the BoNTs into non-neuronal cells, to effect blocking of excessive/pathological secretion of certain molecules from these cells, chimeric receptors containing the toxin binding site can be engineered and be expressed in cells, as exemplified in FIG. 4, in non-neuronal cells, so toxins can bind and enter, and the entry of BoNT blocks the excessive secretion of certain harmful hormones, cytokines, etc. In an alternative embodiment, the receptor binding domain on BoNTs is replaced with a protein fragment, such as a receptor biding domain derived from other toxins/ligands, which binds to one or more receptors that exist in these non-neuronal cells. Such chimeric toxins can target the enzymatic domain of BoNTs into specific cells where the receptors are expressed.

The present invention further provides non-neuronal cell lines that express BoNT toxin receptors and are as sensitive to BoNTs as are neurons. Such cell lines are more stable and easily to handle than primary neuron cell cultures and can facilitate studies of BoNTs and cell-based screening of small molecule inhibitors.

The invention will be more fully understood upon consideration of the following non-limiting example.

EXAMPLES

Materials and Methods

Antibodies, Materials, Mouse Lines

Monoclonal antibodies directed against Syb II (Cl 69.1), Syt I (Syt $I_N$ Ab; Cl 604.4, α-Syt I cytoplasmic domain; Cl 41.1), SV2 (pan-SV2, see J. Cell Biol. 100: 1284-1294), synaptophysin (Cl 7.2) and SNAP-25 (Cl 71.2) were generously provided by R. Jahn (Gottingen, Germany). A human anti-BoNT/B was generously provided by J. Lou and J. Marks (San Francisco, Calif.). Rabbit polyclonal anti-BoNT/A, B and E antibodies and anti-SV2C antibodies were described previously[32, 40]. Guinea pig anti-vesicular glutamate transporter I (vGlut) was purchased from Chemicon (CA). Chicken polyclonal anti-GFP, rabbit polyclonal anti-GFP, mouse monoclonal anti-GFP and rabbit monoclonal anti-LDLR were all purchased from Abcam (MA).

Bovine brain gangliosides were obtained from Matreya LLC (PA). Tetanus neurotoxin was purchased from List Biological Lab (CA).

A Syt I knockout mouse line was obtained from Jackson Laboratory (ME)[57]. Ganglio side knockout mice lack the gene encoding GM2/GD2 synthase (gene symbols: Galgt1)[56] and were obtained from the Consortium for Functional Glycomics (Grant number GM62116). The SV2A, SV2B and SV2A/B knockout mouse lines were described previously[48].

cDNA and Constructs

Rat SV2A, B and C cDNAs were described previously[37-40]. Human low-density lipoprotein receptor (LDLR-2) cDNA was generously provided by S. Blacklow (Boston, Mass.).

Full length SV2A, B and C were subcloned into the Lox-Syn-Syn lentivirus vector (provided by P. Scheiffele, N.Y.). This vector contains two separate neuronal-specific promoters (synapsin promoter). One promoter controls the expression of SV2 isoforms and the other controls expression of EGFP. Point mutations at N-glycosylation sites of SV2A were generated with a QuickChange mutagenesis kit (Stratagene, Calif.).

Chimeric receptors were generated by fusing the 4$^{th}$ luminal domain of each SV2 isoform (residues 468-595 in SV2A, 410-539 in SV2B, 453-580 in SV2C) to the N-terminus of a fragment encoding the transmembrane and cytosolic domain of human LDLR-2 (residues 788-860). In addition, a pre-prolactin signal sequence was fused to the N-terminus of the chimeric receptors[58]. The cDNAs encoding these chimeric receptors were subcloned into the pEGFP-N1 vector to generate GFP tagged receptors, which were used in the experiments described in FIGS. 4b and 4c. These cDNAs were also subcloned into the Lox-Syn-Syn lentivirus vector to generate un-tagged receptors and to produce lentiviruses. Deletion mutations of the chimeric receptors described in FIG. 5a were generated by PCR with addition of a tag derived from the first eleven amino acids of rat Syt I[54].

Neuronal Cell Cultures, Transfection, Viral Infection and Loading Gangliosides

Cultured rat hippocampal neurons were prepared from E18-19 rats. Cultured SV2 KO, Syt I KO and ganglioside deficient hippocampal neurons were prepared from P1 mice. Neurons were plated on poly-D-lysine coated glass coverslips (12 mm) at a density of 50,000/cm$^2$ and cultured in Neurobasal medium supplemented with B-27 (2%) and Glutamax (2 mM). Neurons were generally analyzed at 12-14 DIV.

Transient transfection of neurons was performed at 5 DIV using Lipofectamine 2000 (Invitrogen). Transient transfection of HEK cells was also performed using Lipofectamine 2000. Lentiviral particles were generated as described previously[35]. Viruses were added to neurons at 5 DIV.

To load cells with exogenous gangliosides, ganglioside deficient neurons were incubated in media plus 250 μg/ml of a gangliosides mixture for 12 hrs at 13 DIV.

Immunocytochemistry and Analysis of Neuronal Lysates

The buffers used in FIG. 1a were: control buffer (mM: NaCl 140, KCl 3, KH$_2$PO$_4$ 1.5, Na$_2$HPO$_4$ 8, MgCl$_2$ 0.5), high K$^+$ (same as control buffer but adjusted to 56 mM KCl and 87 mM NaCl, and contains 1 mM CaCl$_2$). Unless specified in the text, hippocampal neurons were generally exposed to toxins in high K$^+$ buffer for 5 min. Neurons were subjected to immunocytochemistry analysis as described previously[35]. All images were collected using a confocal microscope (Olympus FV1000, 60× objective). Scale bars represent 20 μm in all images.

Figure 5:
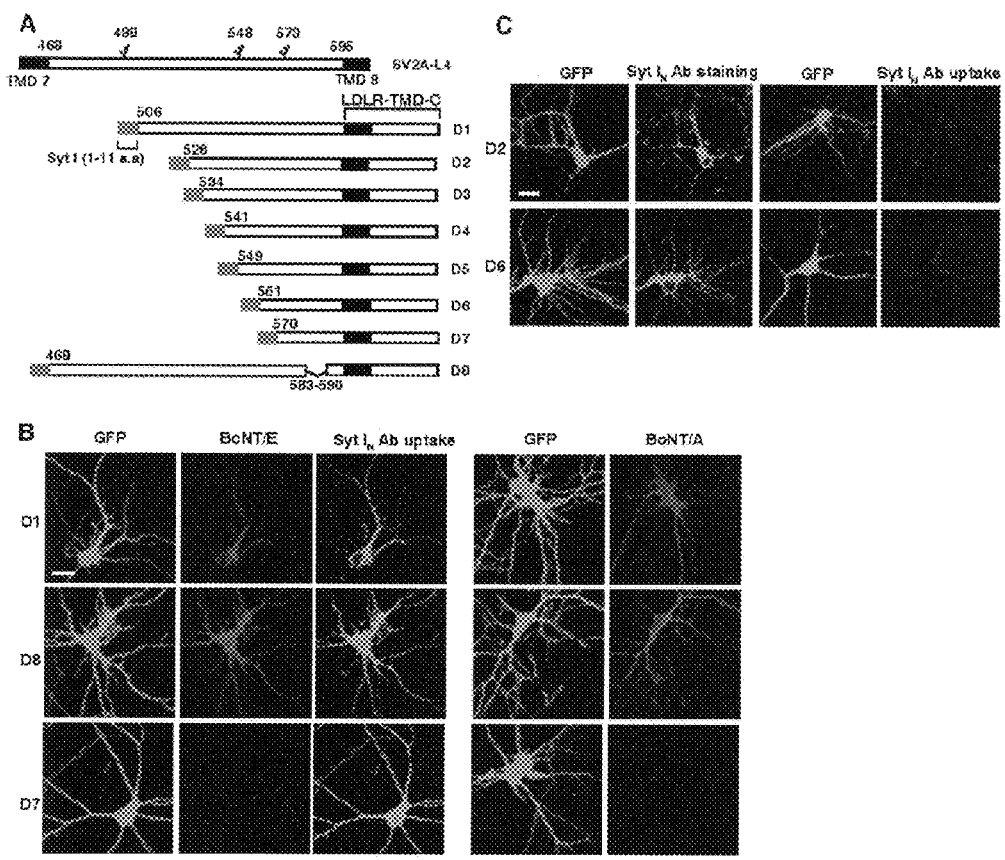
FIG. 5 shows that binding of BoNT/E to SV2A requires the middle portion of the SV2A-L4 domain. a) Schematic drawing of the chimeric receptors containing a series of truncations within the SV2A-L4 domain. In order to monitor the surface exposure of these chimeric receptors, a small tag derived from the first eleven amino acids of rat Syt I was fused to the N-terminus. This tag can mediate the entry of the Syt $I_N$ Ab into neurons when presented on the neuronal cell surface as described in FIG. 1a. b) SV2A/B KO neurons were transfected with the truncation mutants D1, D7 and D8 described in panel a. Transfected neurons were identified by GFP expression, which is under control of a separate promoter within the expression vector. Neurons were exposed to BoNT/E (30 nM) and Syt $I_N$ Ab (1:200) in media for 10 min. Cells were fixed for immunocytochemistry. D1, D7 and D8 mutants all mediated the binding of Syt $I_N$ Ab, indicating that their L4 domains are exposed at the cell surface. D1 and D8 both restored the binding of BoNT/E or BoNT/A (20 nM, right panel) to neurons. D7 failed to restore binding of BoNT/E or BoNT/A. c) Mouse neurons were transfected with the D2 and D6 mutants; representative examples are shown. Left panel: permeabilized neurons were positive for immunostaining with Syt $I_N$ Ab, indicating that these mutants were expressed in transfected neurons. Right panel: Syt $I_N$ Ab uptake experiments were carried out as described in FIG. 1a. The L4 domains of D2 and D6 mutants are all retained inside cells since they failed to take-up Syt $I_N$ Ab.

To monitor the entry of BoNTs into neurons, neurons were briefly exposed to toxins in high K$^+$ buffer (5 min) or in normal culture media (10 min, FIG. 4-5). Neurons were then washed and further incubated in toxin-free media. Neuronal lysates were collected using 100 per well (24-well plate) of the lysate buffer (PBS with 1% Triton X-100, 0.05% SDS and protease inhibitor cocktail (Roche, Calif.)). Lysates were centrifuged for 10 min at maximum speed using a microcentrifuge at 4° C., and the supernatants were subjected to SDS-PAG and immunoblot analysis.

Figure 3:
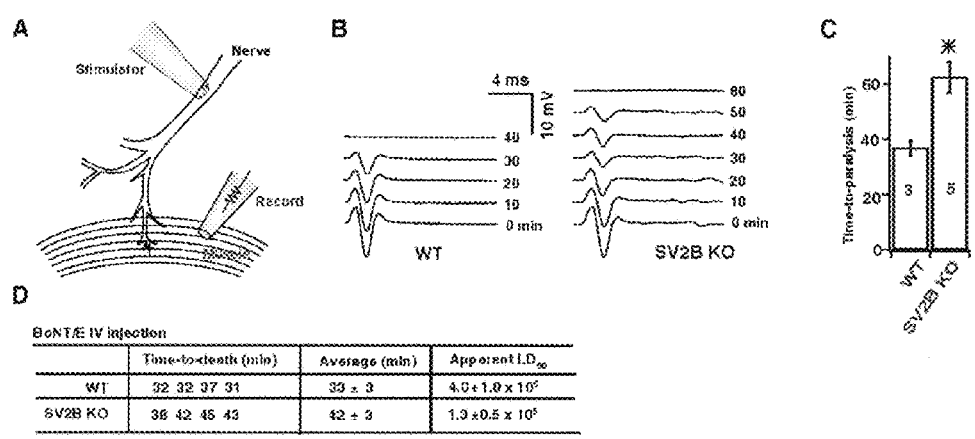
FIG. 3 shows that SV2B KO mice are less sensitive to BoNT/E than WT mice. a) Schematic drawing of the phrenic nerve-diaphragm preparation. Stimulation of the phrenic nerve with a patch pipette triggers muscle contraction. Muscle action potentials were recorded as a readout for contraction (extracellular field potential, EFP). b) Diaphragms, dissected from SV2B KO and WT mice as described in panel a, were exposed to BoNT/E briefly (10 nM, 5 min, at 0 min). EFPs were recorded every two minutes until they became undetectable. "Time-to-paralysis" is the time it takes for the EFP signal to disappear. Representative EFP traces from WT and SV2B KO mice are shown. c) The time-to-paralysis of three WT samples and five SV2B KO samples were determined as described in panel b. Diaphragms from SV2B KO displayed significantly longer (62.4±5.6 mins) time-to-paralysis than diaphragms from WT(36.7±2.7 mins). d) The susceptibility of SV2B(−/−) mice and their WT littermates to BoNT/E was determined using a rapid time-to-death assay. The same amount of BoNT/E was injected into each mouse, and their survival time (time-to-death) was monitored. The average effective toxicity ($LD_{50}$/ml) was estimated from time-to-death data as described previously[32, 59]. SV2B(−/−) mice live significantly longer on average than WT mice. The effective toxicity of BoNT/E in WT mice is about 3-fold greater than in SV2B KO mice.

Diaphragm Preparation, Extracellular Field Potential Measurements, and Rapid BoNT Toxicity Assays in Mice The extracellular field potential (EFP) recording on mouse diaphragm preparations was performed as described previously[52]. Briefly, diaphragms, with the phrenic nerve attached, were excised from mice (P21-P28) and placed immediately into oxygenated Ringer's solution. Diaphragms were pinned down in a recording chamber. The nerve was stimulated with brief stimuli (15-20V/1 msec) every two minutes with a bipolar electrode connected to the voltage output of a Grass Stimulator (SD9). The EFP was recorded using an EPC-10/2 amplifier (HEKA Electronics, Germany) with PATCHMASTER software (HEKA), filtered at 2.9 KHz, and digitized at 5 KHz. The recording electrode was pressed gently against the diaphragm surface (FIG. 3a). The bath was continuously perfused with oxygenated Ringer's solution at a rate of 2-3 ml/min. BoNT/E was added to the bath at a final concentration of 10 nM after the fifth stimulus, while the perfusion was stopped for 5 mins to let the neurons to take-up toxin. The normal Ringer's solution, bathing the nerve-muscle preparation, contained (mM): NaCl 129, KCl 3.0, CaCl$_2$ 2.4, MgSO$_4$ 1.3, NaHCO$_3$ 20, glucose 20, and HEPES 3. The solution was vigorously bubbled with 95% O$_2$/5% CO$_2$ to a pH of 7.4. Data were analyzed using Igor (WaveMetrics, Inc. USA). All experiments were carried out at room temperature.

The effective toxicity of BoNT/E in mice was estimated using the intravenous method described previously[32].

Co-Immunoprecipitation

Co-immunoprecipitation experiments were carried out as described previously[32]. Briefly, BoNT/E (250 nM) was mixed with either rat brain detergent extracts (400 μl, 3 mg/ml, with and without exogenous gangliosides (0.6 mg/ml, FIG. 1c), or cell lysates from HEK cells that express SV2-L4-LDLR receptors (with 0.6 mg/ml exogenous gangliosides, FIG. 4b), for 1 hr at 4° C., and then antibodies were added and were further incubated for 1 hr. Protein G Fast Flow beads (50 μl, Amersham Biosciences) were added last and incubated for additional 1 hr. Beads were washed three times in PBS plus 0.5% Triton X-100. Bound material (25%) was subjected to SDS-PAGE and immunoblot analysis.

Example 1

BoNT/E Enters Neurons Via Recycling Synaptic Vesicles and Co-Immunoprecipitates with SV2

In the first series of experiments, we determined whether BoNT/E enters neurons via synaptic vesicle recycling—the dominant form of membrane recycling that occurs in presynaptic nerve terminals. Synaptic vesicle exocytosis exposes the luminal domains of synaptic vesicle proteins onto the cell surface, where they can serve as toxin binding sites. Exocytosis of synaptic vesicles can be triggered by depolarizing neurons with buffers containing a high concentration of K$^+$, and can be blocked by treating neurons with tetanus neurotoxin (TeNT), which cleaves Syb[4]. Using cultured hippocampal neurons as a model, we found that stimulation of neurons with high K$^+$ resulted in increased binding of BoNT/E (FIG. 1a). Depolarization of neurons with high K$^+$ also increased the binding of an antibody that recognizes the luminal domain of Syt I (Syt I$_N$ Ab), which serves as an internal control to monitor the exposure of luminal domains of synaptic vesicle proteins (FIG. 1a). This treatment also resulted in increased binding of BoNT/E. We also found that pre-treatment of neurons with TeNT diminished the binding of BoNT/E (FIG. 1b). These data indicate that the binding site for BoNT/E is likely to be localized to synaptic vesicles.

The major synaptic vesicle membrane proteins were then screened for their abilities to bind BoNT/E in co-immunoprecipitation experiments. As shown in FIG. 1c, a monoclonal antibody that recognizes all isoforms of SV2 (pan-SV2) was able to co-immunoprecipitate BoNT/E (250 nM) from rat brain detergent (Triton X-100) extracts. Addition of exogenous gangliosides to the brain detergent extract significantly increased the degree of co-immunoprecipitation, suggesting that ganglio sides enhance BoNT/ESV2 interactions. Antibodies against synaptophysin (Syp) and Syt I failed to pull down BoNT/E, indicating BoNT/E specifically interacts with SV2.

Example 2

SV2A or SV2B is Required for the Binding and Entry of BoNT/E into Neurons

Next, we determined whether BoNT/E·SV2 interactions play functional roles in the binding and entry of BoNT/E into neurons. Among the three SV2 isoforms, knockout (KO) mice have been generated for SV2A and B, but not C[47, 48]. Since hippocampal neurons express mainly SV2A and B, neurons from SV2A/B double KO mice serve as a useful loss-of-function model in which we could examine whether the binding and entry of BoNT/E depends on the expression of SV2[35, 40, 49].

Figure 2:
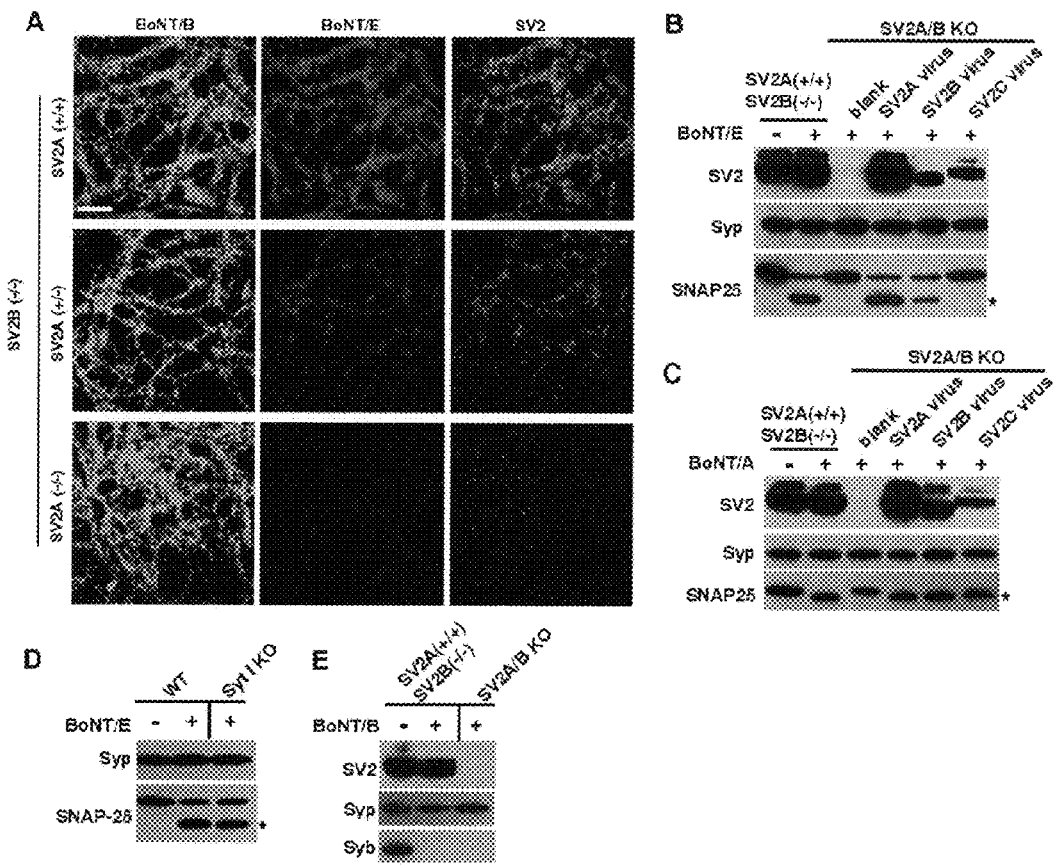
FIG. 2 shows that expression of SV2A or SV2B in neurons is essential for the binding and entry of BoNT/E. a) Hippocampal neurons from littermates with the following genotypes: SV2A(+/+)SV2B(−/−), SV2A(+/−)SV2B(−/−), and SV2A(−/−)SV2B(−/−), were exposed to BoNT/E (30 nM) and BoNT/B (10 nM) simultaneously for 5 min. Triple immunostaining was performed to detect BoNT/B (human anti-BoNT/B), BoNT/E (rabbit polyclonal anti-BoNT/E), and SV2 (mouse monoclonal pan-SV2). Representative images are shown. BoNT/E failed to bind SV2A/B double KO neurons. b) SV2A(+/+)SV2B(−/−) neurons, SV2A/B KO neurons and neurons infected with lentiviruses expressing SV2A, B or C, were briefly exposed to BoNT/E (200 pM, 5 min) and then incubated for 4 hrs in media. Cells were harvested and cell lysates were subjected to SDS-PAGE and immunoblot analysis using antibodies against SV2, Syp and SNAP-25. Cleavage of SNAP-25 was detected using an antibody that recognizes both intact SNAP-25 and the cleavage product (indicated by an asterisk). Syp was assayed as an internal control for loading of cell lysates. BoNT/E failed to enter SV2A/B KO neurons, and entry was rescued by expressing SV2A or SV2B, but not SV2C in neurons. c) Experiments were carried out as described in panel b, except that neurons were exposed to BoNT/A (10 nM, 5 min exposure, 12 hrs incubation). The BoNT/A cleavage product of SNAP-25 is indicated by an asterisk. BoNT/A failed to enter SV2A/B KO neurons, and entry was rescued by expressing SV2A, B or C. d) Hippocampal neurons from Syt I KO mice were exposed to BoNT/E (50 pM) as described in panel b. The degree of cleavage of SNAP-25 by BoNT/E was similar in WT neurons and Syt I KO neurons. e) SV2A(+/+)SV2B(−/−) neurons and SV2A/B KO neurons were assayed for the entry of BoNT/B (10 nM, 5 min exposure, 24 hrs incubation), as described in panel b. The cleavage of Syb by BoNT/B resulted in loss of Syb signals detected using an anti-Syb antibody. Syb, in both SV2A(+/+)SV2B(−/−) and SV2A/B KO neurons, was cleaved by BoNT/B.

SV2A/B double knockout mice were generated by breeding SV2A(+/−)SV2B(−/−) mice with each other. Thus, all of the new-born mice were SV2B(−/−), with varying levels of SV2A: SV2A(+/+), SV2A(+/−), SV2A(−/−). Neurons cultured from these littermates were exposed to BoNT/B and E simultaneously, and toxin-binding was assayed via immunocytochemistry. We found that binding of BoNT/E to SV2A (+/−) neurons was reduced (FIG. 2a, middle panel) compared to SV2A(+/+) neurons (FIG. 2a, upper panel). Binding to SV2A/B double KO neurons was completely abolished (FIG. 2a, lower panel). The binding of BoNT/B, which uses Syt I/II as its protein receptor, to neurons with each genotype remained the same, thus serving as an internal control; neurons lacking SV2 are capable of taking-up BoNTs through synaptic vesicle recycling.

Figure 13:
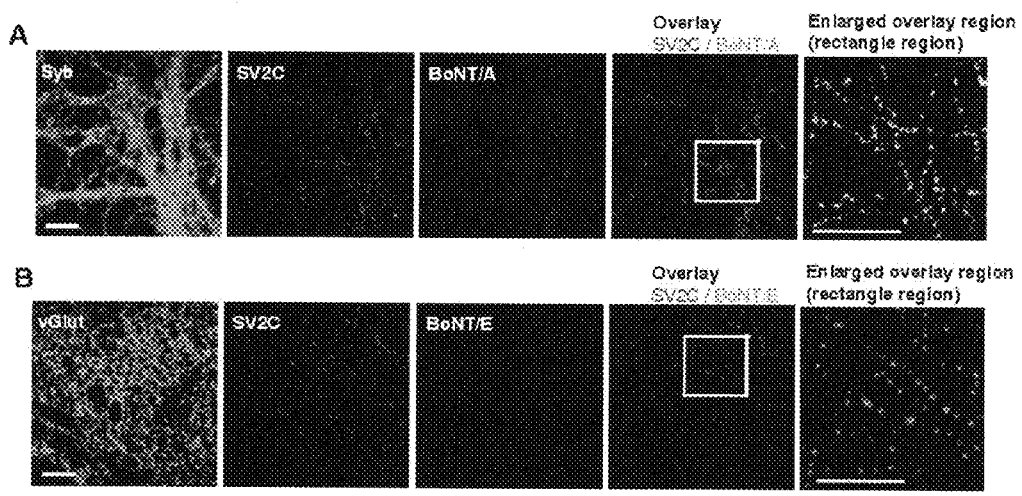
FIG. 13 shows that SV2C is expressed in a subpopulation of synapses in cultured hippocampal neurons and can mediate the binding of BoNT/A but not BoNT/E. a) Cultured hippocampal neurons from SV2 A/B KO mice were exposed to BoNT/A (20 nM) for 5 min in high $K^+$ buffer. Cells were washed, fixed, and immunostained using antibodies against SV2C, BoNT/A and Syb. Syb was used as a marker for synapses. SV2C was detected in a subpopulation of synapses. BoNT/A was found to bind these SV2C-positive synapses. b) Experiments were carried out as described in panel a, except that cells were exposed to BoNT/E (30 nM). vGlut was labeled as a marker for synapses. Binding of BoNT/E to SV2C-positive cells was not detectable.

It was previously reported that a subpopulation of GABAergic nerve terminals of cultured hippocampal neurons may also express SV2C[50]. We also observed that a small fraction of synapses in SV2A/B KO neurons were recognized by the pan-SV2 antibody as well as an SV2C-specific polyconal antibody (FIG. 2a, lower panel, FIG. 13). BoNT/A, which can use all three SV2 isoforms as its receptor, bound to synapses that were stained by the SV2C antibody (FIG. 13a). Interestingly, we did not detect binding of BoNT/E to SV2C-positive synapses (FIG. 13b), suggesting that BoNT/E may not exploit SV2C to enter neurons.

We next examined whether neurons lacking SV2 are resistant to the entry of BoNT/E, and if they are resistant, whether toxin entry can be restored by expressing SV2A, B or C. Functional entry of BoNT/E can be assayed by monitoring the cleavage of its substrate protein SNAP-25. BoNT/E cleaves twenty-six amino acids from the C-terminus of SNAP-25 and the remaining fragment of SNAP-25 can be detected by immunoblotting with SNAP-25 antibodies. SV2A(+/+)SV2B(−/−) neurons from littermates of double KO mice served as controls. Neurons were briefly exposed to BoNT/E (5 min in high K$^+$ buffer) and further incubated for 4 hrs in normal culture media; neuronal lysates were then subjected to SDS-PAGE and immunoblot analysis. SNAP-25 was cleaved by BoNT/E in SV2A(+/+)SV2B(−/−) neurons, while SNAP-25 in SV2A/B double KO neurons was protected from BoNT/E (FIG. 2b).

We then carried out rescue experiments by infecting SV2A/B KO neurons with lentiviruses that express SV2A, B or C. The infection efficiency is >90%, so the expression of SV2A, B or C can be restored in the majority of neurons. As shown in FIG. 2b, expression of SV2A or SV2B, but not SV2C, rescued the entry of BoNT/E as evidenced by the cleavage of SNAP-25. We carried out parallel experiments with BoNT/A (10 nM, 5 min in high K$^+$ buffer, 12 hr incubation). BoNT/A cleaves nine amino acids from the C-terminus of SNAP-25. We found that SV2A, B and C were all able to restore the entry of BoNT/A into SV2A/B KO neurons, as shown by the cleavage of SNAP-25 (FIG. 2c). These findings are consistent with our previous report that SV2A, B and C all can function as receptors for BoNT/A in cells[35].

The inability of BoNT/E to enter neurons lacking SV2 is specific, since BoNT/E can readily enter neurons lacking Syt I, the receptor for BoNT/B and G (FIG. 2d). In addition, BoNT/B, which cleaves Syb, can enter SV2A/B KO neurons (FIG. 2e), further demonstrating that neurons lacking SV2 are able to take-up BoNTs via recycling synaptic vesicles.

Example 3

SV2B KO Mice Display Reduced Sensitivity to BoNT/E

BoNTs cause death in humans and animals by blocking the release of neurotransmitters from motor nerve terminals at the diaphragm[51]. These motor nerve terminals express all three isoforms of SV2[35, 50]. Since SV2C KO mice have not been generated and SV2A KO mice do not survive to adulthood[47, 48], we determined whether motor nerve terminals from SV2B KO mice display decreased susceptibility to BoNT/E compared to motor nerve terminals from WT mice. To test this, we used a phrenic nerve and diaphragm preparation (FIG. 3a)[52]. Stimulation of the phrenic nerve triggers the contraction of the diaphragm muscle, which can be recorded as an extracellular field potential (EFP) (FIG. 3a, b). The EFPs in both WT and SV2B KO last more than 3 hrs in the absence of BoNT/E (data not shown), consistent with a previous report[52]. The EFPs are similar between SV2B KO and WT before adding BoNT/E (FIG. 3b, 0 min). After a brief exposure to BoNT/E (10 nM, 5 min), the EFP decreases over time and eventually disappears, indicating that neurotransmitter release from motor nerve terminals has been blocked by the toxin (FIG. 3b). We define the time it takes for EFPs to fall below the detection threshold as the time-to-paralysis. The average time-to-paralysis in SV2B KO (62.4±5.6 mins) was significantly longer than that in WT (36.7±2.7 mins) (FIG. 3c).

We then carried out whole animal studies to determine the physiological significance of SV2 expression on the action of BoNT/E in vivo. Sensitivity to BoNT/E was assessed with an established rapid assay, in which large doses of toxin are injected intravenously and the survival time (time-to-death) is monitored on a time scale of minutes. This survival time can be converted to intraperitoneal toxicity by using a standard curve[32]. Identical amounts of BoNT/E were injected into SV2B KO and WT littermate control mice. The survival times are shown in FIG. 3d. SV2B knockout mice survived significantly longer than WT littermates (42±3 min versus 33±3 min in average). The toxin was 3-fold more effective in WT mice than in SV2B KO mice (apparent $LD_{50}$, FIG. 3d), indicating that mice lacking SV2B display reduced susceptibility to BoNT/E. The remaining toxicity of BoNT/E in SV2B KO mice was presumably mediated by SV2A and SV2C, which are still expressed in motor nerve terminals[35].

Example 4

The 4$^{th}$ Luminal Domain of SV2A and SV2B Mediates the Binding and Entry of BoNT/E into Neurons We next sought to address the question of whether SV2A and B function as the protein receptors for BoNT/E. To function as a receptor, SV2 must provide a direct binding site for BoNT/E on the neuronal surface. Since the luminal domains of SV2 are the only regions that are exposed to the outside of cells, we determined whether BoNT/E enters cells by binding to the luminal domains of SV2A and B.

SV2 has only one luminal domain of significant length (SV2-L4) (FIG. 4a). This domain contains the binding site for BoNT/A[35, 36]. It has been reported that the L4 domains of SV2A, B and C, purified as GST fusion proteins in *E. coli*, directly bind BoNT/A, but not BoNT/E[35]. However, GST-L4 fragments may lack critical post-translational modifications, such as glycosylation of the putative glycosylation sites within this domain. Thus, it is necessary to test the binding of BoNT/E to the L4 domain that has been expressed in mammalian cells.

In order to exclude other regions of SV2, and to present the L4 domain on the cell surface, we constructed three chimeric receptors by replacing the extracellular domain of the low-density lipoprotein receptor (LDLR) with the L4 domains of SV2A, B or C (FIG. 4a). When expressed in HEK cells, these chimeric receptors displayed complex banding patterns on SDS-PAGE gels. The apparent molecular weight of these bands are higher than the putative size of the chimeras (~55 kDa, including a GFP tag at the C-terminus) (FIG. 4b, left panel), suggesting that these receptors are post-translationally modified. Since there are three putative N-linked glycosylation sites within the L4 domain, and it has been demonstrated that native SV2 is glycosylated[37, 38, 40-42], it is likely that these chimeric receptors are glycosylated within their L4 domains in HEK cells. Interestingly, SV2C displayed a higher molecular weight than SV2A and B, despite the fact that their L4 domains have similar amino acid sequence lengths, suggesting that the glycosylation pattern of SV2C-L4 might be different from SV2A and B.

We first carried out co-immunoprecipitation experiments using a GFP antibody to pull-down chimeric receptors from HEK cell lysates, in the presence of BoNT/A and exogenous gangliosides. As expected, we found that all three chimeric receptors co-immunoprecipitated with BoNT/A (FIG. 4b, right panel). Parallel experiments were carried out using BoNT/E, and we found that BoNT/E was co-immunoprecipitated with the chimeric receptor containing SV2A-L4 (FIG. 4b, right panel). The levels of co-immunoprecipitation of BoNT/E with SV2B-L4 and SV2C-L4 were much less than with SV2A-L4, but were still slightly higher than the control that did not contain SV2-L4 (FIG. 4b, right panel). Lack of significant binding of BoNT/E to SV2C-L4 is consistent with our finding that SV2C failed to rescue the entry of BoNT/E into SV2A/B KO neurons (FIG. 2b).

We next assessed whether the L4 domain alone was sufficient to mediate the binding of BoNT/A and BoNT/E to neurons. The SV2A-L4-LDLR chimeric receptor was expressed in SV2A/B KO neurons. These neurons were exposed to BoNT/A or BoNT/E under resting conditions (10 min in culture media). Binding of BoNT/A and BoNT/E was observed for neurons that expressed the SV2A-L4-LDLR receptor (FIG. 4c).

We then determined whether the chimeric receptors can mediate functional entry of BoNT/A and BoNT/E into neurons. SV2A/B KO neurons were infected with lentiviruses that express chimeric receptors and exposed to BoNT/A (10 nM, FIG. 4d) or BoNT/E (2 nM, FIG. 4e) under resting conditions (10 min in culture media), followed by further incubation for 12 hrs. Cells were harvested and cell lysates were subjected to SDS-PAGE and immunoblot analysis. Cleavage of SNAP-25 by BoNT/A was observed in SV2A/B KO neurons that had been infected with chimeric receptors containing the L4 domains of SV2A, B or C (FIG. 4d), indicating that the L4 domain alone can mediate the entry of toxins into neurons under resting conditions. The entry of BoNT/E into SV2A/B KO neurons was also restored by the expression of the SV2A-L4 or SV2B-L4 receptors, but not by the SV2C-L4 receptor (FIG. 4e), further indicating that BoNT/E can enter neurons via binding to the luminal domain of SV2A or SV2B, but not SV2C.

Consistent with what we have observed for chimeric receptors expressed in HEK cells (FIG. 4b, left panel), the SV2C-L4 chimeric receptor displayed a significantly higher molecular weight compared to the SV2A-L4 or SV2B-L4 receptors (FIG. 4e, please note that the chimeric receptors expressed in neurons are not fused with GFP tags), confirming that glycosylation of SV2C-L4 is somehow distinct from SV2A-L4 and SV2B-L4 in neurons.

Among three SV2-L4 chimeric receptors expressed in HEK cells, SV2A-L4 co-immunoprecipitated much higher levels of BoNT/E than SV2B-L4 and SV2C-L4 (FIG. 4B, right panel), suggesting that SV2A might be the preferred binding partner for BoNT/E. Both SV2B-L4 and SV2C-L4 immunoprecipitated only minimal levels of BoNT/E (FIG. 4B, right panel), indicating their weak association with BoNT/E in vitro. However, when expressed in neurons, it is clear that SV2B-L4, but not SV2C-L4, can mediate the entry of BoNT/E (FIG. 4E). One possible explanation for this apparent discrepancy is that the neuronal surface might provide an optimal environment for SV2B-BoNT/E interactions, as opposed to the artificial conditions that occur in the immunoprecipitates (e.g. the presence of detergents etc).

Example 5

Binding of BoNT/E to SV2A Requires the Middle Portion of the SV2A-L4 Domain

We next attempted to determine the minimal protein sequence within the SV2A-L4 domain that mediates binding of BoNT/E. Because BoNT/E does not bind the recombinant SV2A-L4 domain in vitro, we approached this question by testing binding of BoNT/E to a series LDLR-based chimeric receptors, that contain various truncations and deletions of the SV2A-L4 domain, expressed in neurons (FIG. 5a). Because the truncations of the L4 domain may change the membrane targeting/topology of the chimeric receptors, a tag derived from the first eleven amino acids of rat Syt I was fused to the N-terminus of all the constructs (FIG. 5a). This tag contains the epitope for the Syt $I_N$ antibody and can be used for antibody uptake experiments[54]. Interestingly, the mouse version of Syt I cannot take-up the Syt $I_N$ antibody, possibly due to sequence differences between rat and mouse Syt I (data not shown). These features enabled us to monitor the surface exposure of the chimeric receptors expressed in mouse neurons by testing whether they can take-up the Syt $I_N$ antibody.

Among the eight mutants tested, mutants D1, D7 and D8 were able to take-up the Syt $I_N$ antibody when expressed in SV2A/B KO mouse neurons, indicating that they are targeted correctly to the cell surface (FIG. 5b). When exposed to BoNT/E, mutants D1 and D8 mediated the binding of BoNT/E, while D7 failed to restore binding of BoNT/E to neurons (FIG. 5b). These results indicate that the N-terminal (amino acids 468-505) and the C-terminal portion (583-590) of the SV2A-L4 domain are not required for binding BoNT/E. Similar results were obtained for BoNT/A, which is consistent with our previous findings that the binding site of BoNT/A lies in the middle of the SV2 luminal domain (amino acids 529-566 in SV2C, corresponding to 543-580 in SV2A)[35].

The expression of the D2 and D6 mutants in transfected neurons was detected by immunostaining permeabilized cells with the Syt $I_N$ antibody (FIG. 5c, left panel). However, both mutants failed to take-up the Syt $I_N$ antibody in the live-cell up-take experiments, indicating that their L4 domains were not exposed to the cell surface (FIG. 5c, right panel). Similar results were observed for other mutants (D3, D4 and D5, data not shown). The mistargeting of these mutants prevented us from further mapping the binding site for BoNT/E within the luminal domain of SV2A.

Example 6

Figure 6:
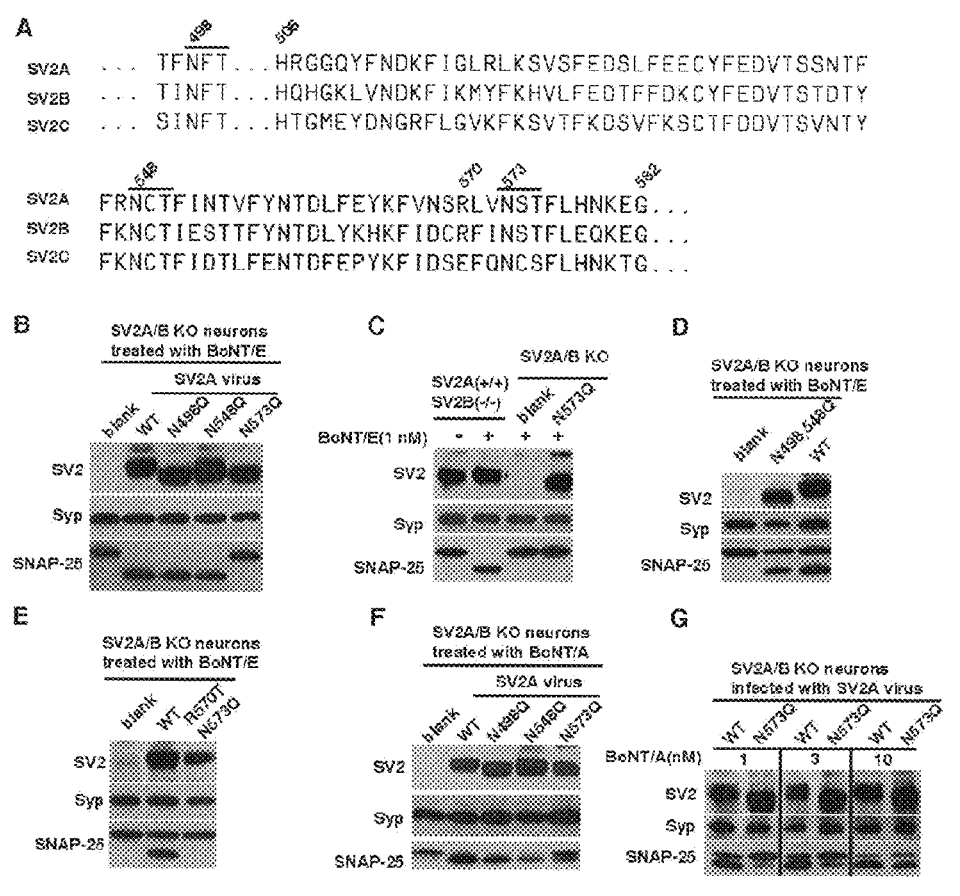

Glycosylation at the 3rd N-Linked Glycosylation Site of the SV2A-L4 Domain is Needed for the Entry of BoNT/E, and Enhances the Entry of BoNT/A, into Neurons SV2 is a major synaptic vesicle proteoglycan and N-linked glycosylation was shown to be the predominant, if not exclusive, form of modification[37, 38, 40-42]. SV2 has only three putative N-linked glycosylation sites (N-X-S/T consensus sequence, where X can be any amino acid except proline), all of which are localized within the L4 domain (FIG. 4a, 6a). Two of the three glycosylation sites are localized within the binding site for BoNT/E (N548 and N573 in SV2A). We therefore examined whether glycosylation of the SV2A-L4 domain affects the binding of BoNT/E.

The glycosylation patterns and the structure of the N-glycans of SV2 have not been elucidated. On SDS-PAGE gels, SV2 from rat brain detergent extracts runs as a smear of bands from ~100 kDa to more than 250 kDa, indicating heterogeneous glycosylation. Attempts to remove all of the N-glycans in SV2 with PNGase F, under non-denaturing conditions, were unsuccessful, possibly because the N-glycosylation sites are not fully accessible to this enzyme (data not shown)[42]. This prevented us from testing the effect of de-glycosylation on binding of BoNT/E in vitro. Thus, we relied on testing whether the disruption of the glycosylation of SV2, through site-directed mutagenesis, affects the binding of BoNT/E to neurons.

Each of three N-linked glycosylation sites in SV2A-L4 was disrupted by a point mutation (N to Q). These mutants were expressed in SV2A/B KO neurons using lentiviruses and the entry of BoNT/E into these neurons was detected by assaying for the cleavage of SNAP-25 by immunoblot analysis. As shown in FIG. 6b, all three SV2 mutants ran at a lower apparent molecular weight compared to WT SV2 on SDS-PAGE gels, indicating that all three putative N-linked glycosylation sites are glycosylated in neurons. Mutations at the first or the second glycosylation sites (N498Q, N548Q) did not affect the entry of BoNT/E, while mutation at the third glycosylation site (N573Q) completely abolished the entry of BoNT/E as evidenced by the lack of cleavage of SNAP-25 (FIG. 6b). Even when the toxin concentration was increased 5-fold (1 nM, FIG. 6c), cleavage of SNAP-25 was not observed in neurons expressing the N573Q mutant form of SV2A.

We next assayed whether glycosylation at the third site alone is sufficient to mediate the entry of BoNT/E. SV2A, harboring mutations at both the first and the second glycosylation sites (N498,548Q), was expressed in SV2A/B KO neurons. As shown in FIG. 6d, the N498,548Q mutant was capable of mediating the entry of BoNT/E as monitored by the cleavage of SNAP-25. This finding demonstrated that glycosylation at the N573 position alone, among three glycosylation sites, is sufficient for SV2 to mediate the entry of BoNT/E.

We also created an SV2A mutant in which we generated a new N-linked glycosylation site in the SV2A(N573Q) mutant through a point mutation at a nearby site (R570T); in effect this shifted the N-linked glycosylation site from N573 to N568. Once expressed in neurons, this mutant (R570T, N573Q) had a similar molecular weight as WT SV2A (FIG. 6e), indicating that the new glycosylation site is in fact glycosylated. However, this mutant failed to mediate the entry of BoNT/E (FIG. 6e), suggesting that the loss of entry of BoNT/E, due to loss of glycosylation at N573 site, cannot be rescued by compensatory glycosylation at a nearby site.

Because the BoNT/A binding site also includes the second and the third glycosylation sites of SV2, we assayed whether abolishing these glycosylation sites affects the entry of BoNT/A into neurons. As shown in FIG. 6f, entry of BoNT/A was not affected by mutations at the first and the second glycosylation sites, while the cleavage of SNAP-25 was reduced, but not completely blocked, by mutating the third glycosylation site. To confirm these findings, we titrated the concentration of BoNT/A and compared the cleavage of SNAP-25 in neurons expressing WT SV2 and the SV2A (N573Q) mutant (FIG. 6g). At low concentrations of BoNT/A (1-3 nM), less cleavage of SNAP-25 was observed in neurons that expressed the N573Q mutant compared to neurons that expressed WT SV2A; at higher [BoNT/A] (10 nM), this difference became negligible. These results indicate that neurons expressing WT SV2A have a higher sensitivity to BoNT/A than neurons that express the SV2A(N573Q) mutant, suggesting that glycosylation of the N573 site is not essential for, but may enhance, the entry of BoNT/A mediated by SV2A.

Figure 14:
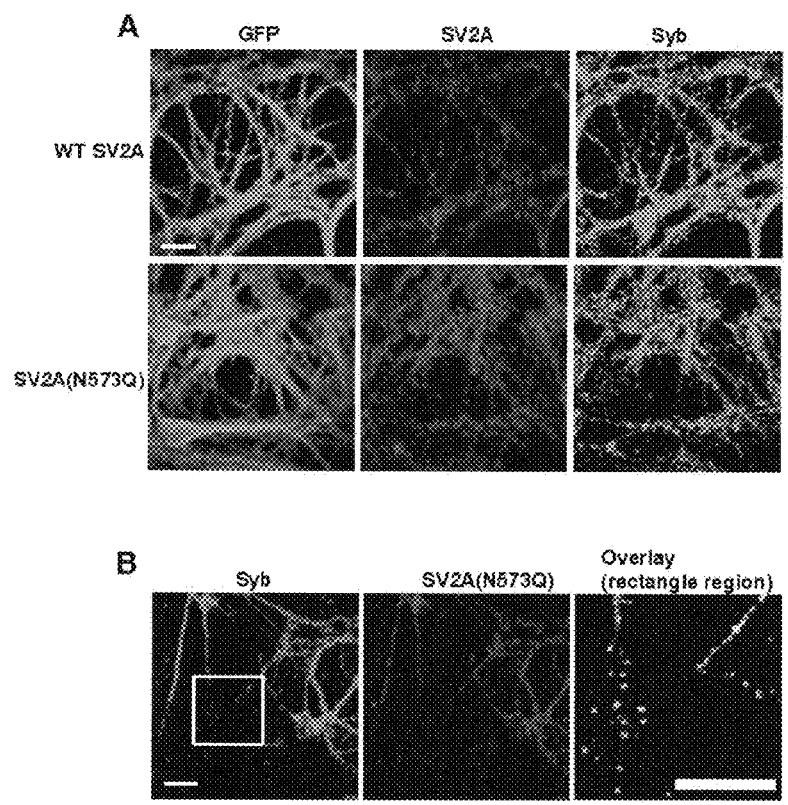
FIG. 14 shows that SV2A(N573Q) was expressed in neurons at similar levels as WT SV2A and co-localized with the synaptic vesicle marker Syb. a) Cultured SV2A/B KO neurons were infected with lentiviruses that express SV2A(WT) or SV2A(N573Q), respectively. Cells were fixed and immunostained with antibodies against GFP, SV2A, and Syb. GFP is expressed under control of a separate promotor in the virus vector, and served to indicate that almost all neurons were infected. Representative images are shown. b) Images were acquired as described in panel a. The rectangle region is enlarged to show the co-localization between Syb and SV2A (N573Q).

Importantly, the finding that SV2A(N573Q) can mediate the entry of BoNT/A into neurons demonstrated that loss of glycosylation at the third N-linked glycosylation site, through a point mutation, does not alter the expression or targeting of SV2A in neurons. This finding is further supported by our observation that SV2A(N573Q), expressed via lentiviral infection, targeted to synapses in neurons, as evidenced by the high degree of co-localization with the synaptic marker Syb II (FIG. 14).

While not willing to be bound by any discussion or speculation on mechanism, it is believed that there are two possibilities for the importance of N-linked glycosylation at position N573 of SV2A. First, glycosylation might be critical for helping the SV2-L4 domain fold into a certain structure that is essential for BoNT/E recognition and that also enhances the binding of BoNT/A. Interestingly, the L4 domain has an unusually high percentage of hydrophobic amino acids, particularly phenylalanine, spaced every fifth position from each other[37, 38, 40]. This feature will probably require the L4 domain to fold in a manner that minimizes the exposure of hydrophobic surfaces. Alternatively, the N-glycan at N573 might contain specific structural groups that can bind directly to BoNT/E and BoNT/A. Analysis of the structure of this N-glycan is needed in order to determine whether there is a specific binding site for BoNT/E and A within the N-glycan itself.

Example 7

Gangliosides are Essential for the Binding and Entry of BoNT/E into Neurons

Figure 7:
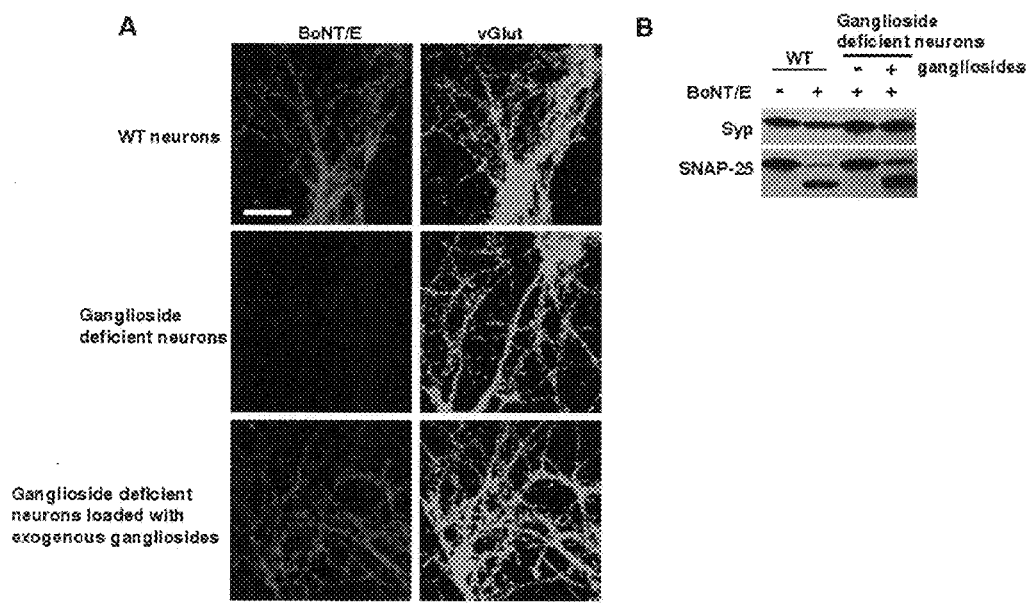
FIG. 7 indicates that gangliosides are essential for the binding and entry of BoNT/E into neurons. a) Cultured WT and ganglioside deficient neurons were exposed to BoNT/E (30 nM) as described in FIG. 1a. Ganglioside deficient neurons, pre-loaded with exogenous gangliosides (250 μg/ml ganglioside mixture, 12 hrs), were assayed in parallel. Immunostaining was carried out using antibodies against BoNT/E and vGlut. Binding of BoNT/E to ganglioside deficient neurons was abolished but was rescued by loading neurons with exogenous gangliosides. b) Cultured WT and ganglioside deficient neurons were exposed to BoNT/E (200 pM) as described in FIG. 2b. Ganglioside deficient neurons, pre-loaded with exogenous gangliosides, were assayed in parallel. Neurons were harvested and subjected to immunoblot analysis. In ganglioside deficient neurons, SNAP-25 was protected from BoNT/E, while loading these neurons with exogenous gangliosides resulted in entry of BoNT/E, as monitored by the cleavage of SNAP-25.

Finally, we sought to address whether gangliosides are essential co-receptors for the binding and entry of BoNT/E into neurons. We found BoNT/E failed to bind hippocampal neurons cultured from mice lacking gangliosides[5,6], binding was restored by loading exogenous gangliosides into neuronal membranes (FIG. 7a). Furthermore, BoNT/E failed to enter ganglioside deficient neurons as demonstrated by the lack of cleavage of SNAP-25 (FIG. 7b). Loading ganglio side deficient neurons with exogenous ganglio sides rescued the entry of BoNT/E, resulting in the cleavage of SNAP-25 (FIG. 7b). Together, these data demonstrate that gangliosides are essential for the binding and entry of BoNT/E into neurons.

Example 8

Chimeric Receptors are able to Mediate the Entry of BoNT/A and B into Non-Neuronal Cells 1. LDL-PC12: Chimeric receptors that contain the luminal domains of Syt 11 or SV2 mediate binding and entry of BoNT/B or BoNT/A, respectively, into PC12 cells.

Figure 9:
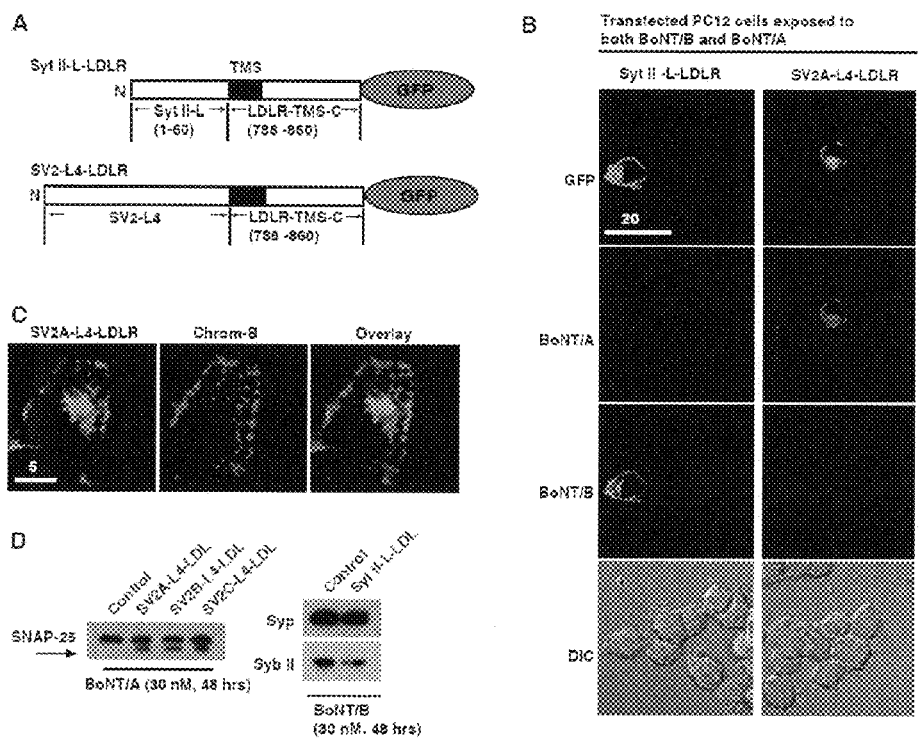
FIG. 9 shows that chimeric receptors that contain the luminal domains of Syt II or SV2 mediate binding and entry of BoNT/B or BoNT/B, respectively, into PC12 cells. (A) Schematic drawings of chimeric receptors comprising luminal domains of Syt II or SV2A/B/C and the transmembrane and cytosolic domains of the LDL-receptor. (B) PC 12 cells transfected with either Syt II-L-LDLR or SV2A-L4-LDLR and exposed to BoNT/A (30 nM) and BoNT/B (10 nM) for 30 minutes. (C) Immunostaining for Chromogranin B shows that SV2A-L4-LDLR does not localize to secretory vesicles. (D) Cells of a SV2A knock-down PC12 cell line were transfected with receptors containing luminal domains of SV2A, SV2B, or SV2C, and exposed to BoNT/A.

As shown in FIG. 9, chimeric receptors comprising the extracellular domain of low-density lipoprotein receptor (LDLR) with the toxin binding sites of SV2 or Syt II are able to mediate the entry of BoNT/A and B into non-neuronal cells.

FIG. 9A is schematic drawings of the chimeric receptors, which are composed of the luminal domains of Syt II or SV2A/B/C, and the transmembrane and cytosolic domains of the LDL-receptor. In addition, a GFP tag was fused to the C-terminus of the chimeric receptor to visualize transfected cells.

PC12 cells were transfected with either Syt II-L-LDLR or SV2A-L4-LDLR (FIG. 9B). Cells were exposed to BoNT/A (30 nM) and BoNT/B (10 nM) for 30 min in normal culture media. Immunostaining was then carried out for BoNT/A and BoNT/B. Expression of Syt II-L-LDLR mediated the entry of BoNT/B, and expression of SV2A-L4-LDLR mediated the entry of BoNT/A into PC12 cells under resting conditions.

PC12 cells transfected with SV2A-L4-LDLR were fixed and immunostained for Chromogranin B, a secretory vesicle marker. An image of a representative cell is enlarged; SV2A-L4-LDLR does not localize to secretory vesicles (FIG. 9C).

Cells of an SV2A knock-down PC12 cell line (Dong et al., 2006) were transfected with chimeric receptors containing the luminal domains of SV2A, SV2B or SV2C. Cells were exposed to BoNT/A (30 nM, 48 hrs in media) and harvested. Cell lysates were analyzed by western blot using SNAP-25 antibody (CI 71.1). The cleavage of SNAP-25 by BoNT/A generated a smaller fragment, which is indicated by an arrow (FIG. 9D, Left panel). WT PC12 cells were transfected with Syt II-L-LDLR receptor and exposed to BoNT/B (30 nM, 48 hrs in media). Cells were harvested and cell lysates were analyzed by western blot using Syb II antibody. The cleavage of Syb II reduced the amount of Syb II that can be detected by this antibody (FIG. 9D, Right panel).

Example 9

Figure 10:
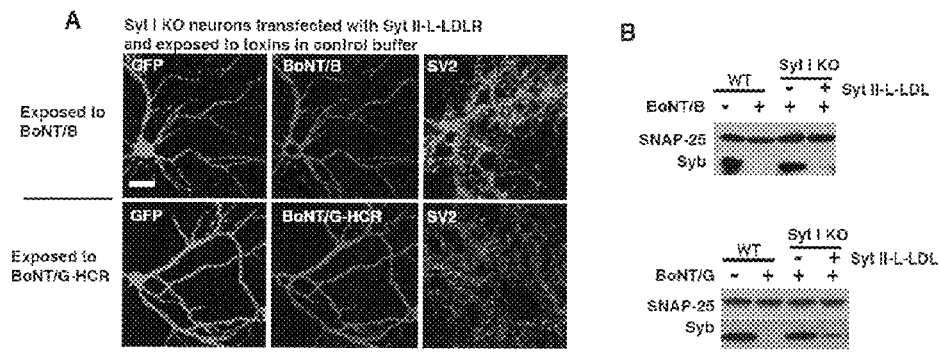
FIG. 10 shows that expression of Syt II-L-LDLR chimeric receptors restores the entry of BoNT/B or G into Syt I KO neurons. (A) Syt I knockout neurons were transfected with Syt II-L-LDLR chimeric receptor and exposed to BoNT/B (10 nM, upper panel) or BoNT/G (receptor binding domain, 100 nm, lower panel). (B) Syt I KO neurons were infected with lentivirus that express Syt II-L-LDLR and exposed to BoNT/B (10 nM) or BoNT/G (30 nM).

Expression of Syt II-L-LDLR Chimeric Receptors Restores the Entry of BoNT/B or G into Syt I KO Neurons Syt I knockout neurons were transfected with Syt II—L-LDLR chimeric receptor, and exposed to BoNT/B (10 nM, upper panel) or BoNT/G-HCR (receptor binding domain, 100 nM, lower panel). Cells were washed and fixed. GFP signals label the transfected cells. SV2 was also detected to label all synapses. Expression of Syt II-L-LDLR restored the binding of BoNT/B and BoNT/G-HCR to Syt I KO neurons (FIG. 10A).

Syt I KO neurons were infected with lentivirus that express Syt II-L-LDLR. These neurons were exposed to BoNT/B (10 nM, 5 min in High K$^+$ buffer) or BoNT/G (30 nM, 5 min in High K+ buffer). Cells were further incubated for 24 hrs. Cell lysates were harvested and subjected to western blot analysis. Expression of Syt II-L-LDLR chimeric receptors restored the entry of BoNT/B or G into Syt I KO neurons (FIG. 10B).

Example 10

Figure 11:
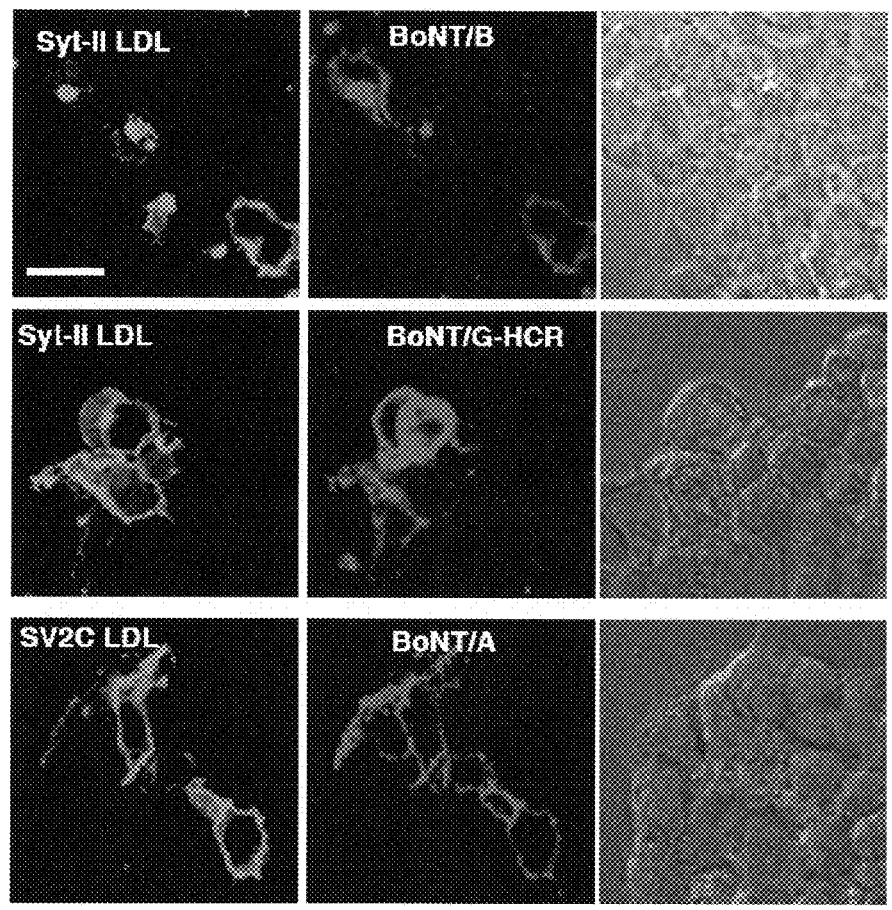
FIG. 11 shows that expression of chimeric receptors results in the binding of BoNT/B, G-HCR or BoNT/A to HEK cells

Expression of Chimeric Receptors Results in the Binding of BoNT/B, G-HCR or BoNT/A to HEK Cells HEK cells were transfected with either Syt II-L-LDLR chimeric receptor or SV2C-L4-LDLR chimeric receptors and exposed to BoNT/B (10 nM), BoNT/G-HCR (100 nM) or BoNT/A (20 nM). Cells were washed and fixed. GFP labels transfected cells. Expression of chimeric receptors resulted in the binding of BoNT/B, G-HCR or BoNT/A to HEK cells, respectively (FIG. 11).

Example 11

Figure 12:
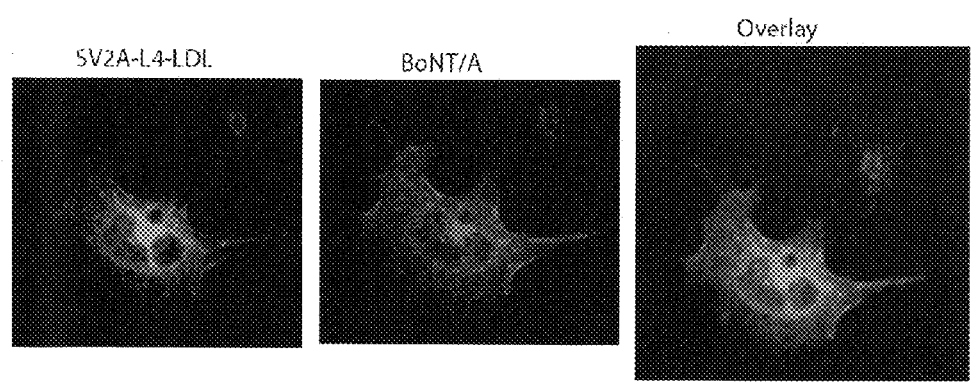
FIG. 12 shows that expression of SV2A-L4-LDLR chimeric receptor results in the entry of BoNT/A into COS-7 cells.

Expression of SV2A-L4-LDLR Chimeric Receptor Results in the Entry of BoNT/A into COS-7 Cells COS-7 cells were transfected with SV2A-L4-LDLR chimeric receptor. Cells were exposed to BoNT/A (20 nM, 30 min in culture media). Cells were washed and fixed. Expression of SV2A-L4-LDLR chimeric receptor resulted in the entry of BoNT/A into COS-7 cells (FIG. 12).

REFERENCES

1. Schiavo, G., Matteoli, M. & Montecucco, C. Neurotoxins affecting neuroexocytosis. *Physiol Rev* 80, 717-766 (2000).
2. Simpson, L. L. Identification of the major steps in botulinum toxin action. *Annu Rev Pharmacol Toxicol* 44, 167-193 (2004).
3. Arnon, S. S. et al. Botulinum toxin as a biological weapon: medical and public health management. *Jama* 285, 1059-1070 (2001).
4. Schiavo, G. et al. Tetanus and botulinum-B neurotoxins block neurotransmitter release by proteolytic cleavage of synaptobrevin. *Nature* 359, 832-835 (1992).
5. Blasi, J. et al. Botulinum neurotoxin C1 blocks neurotransmitter release by means of cleaving HPC-1/syntaxin. *Embo J* 12, 4821-4828 (1993).
6. Schiavo, G. et al. Identification of the nerve terminal targets of botulinum neurotoxin serotypes A, D, and E. *J Biol Chem* 268, 23784-23787 (1993).
7. Schiavo, G., Shone, C. C., Rossetto, O., Alexander, F. C. & Montecucco, C. *Botulinum* neurotoxin serotype F is a zinc endopeptidase specific for VAMP/synaptobrevin. *J Biol Chem* 268, 11516-11519 (1993).
8. Blasi, J. et al. Botulinum neurotoxin A selectively cleaves the synaptic protein SNAP-25. *Nature* 365, 160-163 (1993).
9. Schiavo, G. et al. Botulinum G neurotoxin cleaves VAMP/synaptobrevin at a single Ala-Ala peptide bond. *J Biol Chem* 269, 20213-20216 (1994).

10. Rothman, J. E. & Warren, G. Implications of the SNARE hypothesis for intracellular membrane topology and dynamics. *Curr Biol* 4, 220-233 (1994).
11. Jahn, R. & Sudhof, T. C. Membrane fusion and exocytosis. *Annu Rev Biochem* 68, 863-911 (1999).
12. Jahn, R. & Scheller, R. H. SNAREs—engines for membrane fusion. *Nat Rev Mol Cell Biol* 7, 631-643 (2006).
13. Johnson, E. A. Clostridial toxins as therapeutic agents: benefits of nature's most toxic proteins. *Annu Rev Microbiol* 53, 551-575 (1999).
14. Aoki, K. R. Botulinum toxin: a successful therapeutic protein. *Curr Med Chem* 11, 3085-3092 (2004).
15. Dodick, D., Blumenfeld, A. & Silberstein, S. D. Botulinum neurotoxin for the treatment of migraine and other primary headache disorders. *Clin Dermatol* 22, 76-81 (2004).
16. Montecucco, C. & Molgo, J. Botulinal neurotoxins: revival of an old killer. *Curr Opin Pharmacol* 5, 274-279 (2005).
17. Verderio, C. et al. Entering neurons: botulinum toxins and synaptic vesicle recycling. *EMBO Rep* 7, 995-999 (2006).
18. Montecucco, C. How do tetanus and botulinum toxins bind to neuronal membranes? *TIBS,* 314-317 (1986).
19. Kitamura, M., Iwamori, M. & Nagai, Y. Interaction between *Clostridium botulinum* neurotoxin and gangliosides. *Biochim Biophys Acta* 628, 328-335 (1980).
20. Kozaki, S., Kamata, Y., Watarai, S., Nishiki, T. & Mochida, S. Ganglioside GT1b as a complementary receptor component for *Clostridium botulinum* neurotoxins. *Microb Pathog* 25, 91-99 (1998).
21. Rummel, A., Mahrhold, S., Bigalke, H. & Binz, T. The HCC-domain of botulinum neurotoxins A and B exhibits a singular ganglioside binding site displaying serotype specific carbohydrate interaction. *Mol Microbiol* 51, 631-643 (2004).
22. Yowler, B. C. & Schengrund, C. L. Botulinum neurotoxin A changes conformation upon binding to ganglioside GT1b. *Biochemistry* 43, 9725-9731 (2004).
23. Yowler, B. C., Kensinger, R. D. & Schengrund, C. L. Botulinum neurotoxin A activity is dependent upon the presence of specific gangliosides in neuroblastoma cells expressing synaptotagmin I. *J Biol Chem* 277, 32815-32819 (2002).
24. Chai, Q. et al. Structural basis of cell surface receptor recognition by botulinum neurotoxin B. *Nature* 444, 1096-1100 (2006).
25. Dong, M., Tepp, W. H., Liu, H., Johnson, E. A. & Chapman, E. R. Mechanism of botulinum neurotoxin B and G entry into hippocampal neurons. *The Journal of cell biology* 179, 1511-1522 (2007).
26. Kitamura, M., Takamiya, K., Aizawa, S. & Furukawa, K. Gangliosides are the binding substances in neural cells for tetanus and botulinum toxins in mice. *Biochim Biophys Acta* 1441, 1-3 (1999).
27. Tsukamoto, K. et al. Binding of *Clostridium botulinum* type C and D neurotoxins to ganglioside and phospholipid. Novel insights into the receptor for clostridial neurotoxins. *J Biol Chem* 280, 35164-35171 (2005).
28. Bullens, R. W. et al. Complex gangliosides at the neuromuscular junction are membrane receptors for autoantibodies and botulinum neurotoxin but redundant for normal synaptic function. *J Neurosci* 22, 6876-6884 (2002).
29. Rummel, A. et al. Identification of the protein receptor binding site of botulinum neurotoxins B and G proves the double-receptor concept. *Proceedings of the National Academy of Sciences of the United States of America* 104, 359-364 (2007).
30. Nishiki, T. et al. Identification of protein receptor for *Clostridium botulinum* type B neurotoxin in rat brain synaptosomes. *J Biol Chem* 269, 10498-10503 (1994).
31. Nishiki, T. et al. The high-affinity binding of *Clostridium botulinum* type B neurotoxin to synaptotagmin II associated with gangliosides GT1b/GD1a. *FEBS Lett* 378, 253-257 (1996).
32. Dong, M. et al. Synaptotagmins I and II mediate entry of botulinum neurotoxin B into cells. *The Journal of cell biology* 162, 1293-1303 (2003).
33. Rummel, A., Karnath, T., Henke, T., Bigalke, H. & Binz, T. Synaptotagmins I and II act as nerve cell receptors for botulinum neurotoxin G. *J Biol Chem* 279, 30865-30870 (2004).
34. Jin, R., Rummel, A., Binz, T. & Brunger, A. T. Botulinum neurotoxin B recognizes its protein receptor with high affinity and specificity. *Nature* 444, 1092-1095 (2006).
35. Dong, M. et al. SV2 is the protein receptor for botulinum neurotoxin A. *Science* 312, 592-596 (2006).
36. Mahrhold, S., Rummel, A., Bigalke, H., Davletov, B. & Binz, T. The synaptic vesicle protein 2C mediates the uptake of botulinum neurotoxin A into phrenic nerves. *FEBS Lett* 580, 2011-2014 (2006).
37. Bajjalieh, S. M., Peterson, K., Shinghal, R. & Scheller, R. H. SV2, a brain synaptic vesicle protein homologous to bacterial transporters. *Science* 257, 1271-1273 (1992).
38. Feany, M. B., Lee, S., Edwards, R. H. & Buckley, K. M. The synaptic vesicle protein SV2 is a novel type of transmembrane transporter. *Cell* 70, 861-867 (1992).
39. Bajjalieh, S. M., Peterson, K., Linial, M. & Scheller, R. H. Brain contains two forms of synaptic vesicle protein 2. *Proceedings of the National Academy of Sciences of the United States of America* 90, 2150-2154 (1993).
40. Janz, R. & Sudhof, T. C. SV2C is a synaptic vesicle protein with an unusually restricted localization: anatomy of a synaptic vesicle protein family. *Neuroscience* 94, 1279-1290 (1999).
41. Buckley, K. & Kelly, R. B. Identification of a transmembrane glycoprotein specific for secretory vesicles of neural and endocrine cells. *The Journal of cell biology* 100, 1284-1294 (1985).
42. Scranton, T. W., Iwata, M. & Carlson, S. S. The SV2 protein of synaptic vesicles is a keratan sulfate proteoglycan. *Journal of neurochemistry* 61, 29-44 (1993).
43. Sobel, J. Botulism. *Clin Infect Dis* 41, 1167-1173 (2005).
44. Yule, A. M., Austin, J. W., Barker, I. K., Cadieux, B. & Moccia, R. D. Persistence of *Clostridium botulinum* neurotoxin type E in tissues from selected freshwater fish species: implications to public health. *Journal of food protection* 69, 1164-1167 (2006).
45. Lawrence, G., Wang, J., Chion, C. K., Aoki, K. R. & Dolly, J. O. Two protein trafficking processes at motor nerve endings unveiled by botulinum neurotoxin E. *The Journal of pharmacology and experimental therapeutics* 320, 410-418 (2007).
46. Keller, J. E., Cai, F. & Neale, E. A. Uptake of botulinum neurotoxin into cultured neurons. *Biochemistry* 43, 526-532 (2004).
47. Crowder, K. M. et al. Abnormal neurotransmission in mice lacking synaptic vesicle protein 2A (SV2A). *Proceedings of the National Academy of Sciences of the United States of America* 96, 15268-15273 (1999).
48. Janz, R., Goda, Y., Geppert, M., Missler, M. & Sudhof, T. C. SV2A and SV2B function as redundant Ca2+ regulators in neurotransmitter release. *Neuron* 24, 1003-1016 (1999).

49. Bajjalieh, S. M., Frantz, G. D., Weimann, J. M., McConnell, S. K. & Scheller, R. H. Differential expression of synaptic vesicle protein 2 (SV2) isoforms. *J Neurosci* 14, 5223-5235 (1994).
50. Verderio, C. et al. Traffic of botulinum toxins A and E in excitatory and inhibitory neurons. *Traffic (Copenhagen, Denmark)* 8, 142-153 (2007).
51. Dolly, J. O., Black, J., Williams, R. S. & Melling, J. Acceptors for botulinum neurotoxin reside on motor nerve terminals and mediate its internalization. *Nature* 307, 457-460 (1984).
52. Zhou, L., Zhang, C. L., Messing, A. & Chiu, S. Y. Temperature-sensitive neuromuscular transmission in Kv1.1 null mice: role of potassium channels under the myelin sheath in young nerves. *J Neurosci* 18, 7200-7215 (1998).
53. Chen, W. J., Goldstein, J. L. & Brown, M. S. NPXY, a sequence often found in cytoplasmic tails, is required for coated pit-mediated internalization of the low density lipoprotein receptor. *J Biol Chem* 265, 3116-3123 (1990).
54. Chapman, E. R. & Jahn, R. Calcium-dependent interaction of the cytoplasmic region of synaptotagmin with membranes. Autonomous function of a single C2-homologous domain. *J Biol Chem* 269, 5735-5741 (1994).
55. Baldwin, M. R. & Barbieri, J. T. Association of botulinum neurotoxin serotypes a and B with synaptic vesicle protein complexes. *Biochemistry* 46, 3200-3210 (2007).
56. Liu, Y. et al. A genetic model of substrate deprivation therapy for a glycosphingolipid storage disorder. *J Clin Invest* 103, 497-505 (1999).
57. Geppert, M. et al. Synaptotagmin I: a major Ca2+ sensor for transmitter release at a central synapse. *Cell* 79, 717-727 (1994).
58. Miesenbock, G. & Rothman, J. E. Patterns of synaptic activity in neural networks recorded by light emission from synaptolucins. *Proceedings of the National Academy of Sciences of the United States of America* 94, 3402-3407 (1997).
59. Malizio, C. G., M C.; Johnson, E A. Purification of *Clostridium botulinum* Type A Neurotoxin, in *Bacterial Toxins Methods and Protocols* Vol. 145. (ed. O. Holst) 27-39 (Humana Press, 2000).

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. All references cited hereinabove and/or listed below are hereby expressly incorporated by reference.

What is claimed is:

1. A method for reducing *botulinum* neurotoxin E (BoNT/E) toxicity in an animal comprising administering to the animal a synaptic vesicle membrane protein 2A (SV2A) or synaptic vesicle membrane protein 2B (SV2B) polypeptide, wherein the SV2A polypeptide is at least 90% identical to SEQ ID NO:4, and has a glycosylated N residue at position 573, and wherein the SV2B polypeptide comprises the amino acid sequence set forth as SEQ ID NO:7 and has a glycosylated N at position 516.

2. The method of claim 1, wherein the animal is a mammal.

3. The method of claim 2, wherein the mammal is a human.

4. The method of claim 1, wherein the SV2A polypeptide comprises an amino acid sequence that is at least 90% identical to residues 506-582 of the amino acid sequence set forth as SEQ ID NO:4.

5. The method of claim 1, wherein the SV2A polypeptide comprises the sequence set forth as residues 506-582 of the amino acid sequence set forth as SEQ ID NO:4.

6. The method of claim 1, wherein the polypeptide is a full length SV2A or SV2B polypeptide.

\* \* \* \* \*